United States Patent
Whalley et al.

(10) Patent No.: US 12,263,139 B2
(45) Date of Patent: Apr. 1, 2025

(54) USE OF CANNABIDIOL IN THE TREATMENT OF TUBEROUS SCLEROSIS COMPLEX

(71) Applicant: Jazz Pharmaceuticals Research UK Limited, Kent (GB)

(72) Inventors: Benjamin Whalley, Cambridge (GB); William Hind, Cambridge (GB); Royston Gray, Cambridge (GB); Michael Bazelot, Cambridge (GB); Ines De Silva Serra, Reading (GB); Claire Williams, Reading (GB); Andrew Tee, Cambridge (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 0 days.

(21) Appl. No.: 18/161,603

(22) Filed: Jan. 30, 2023

(65) Prior Publication Data
US 2023/0301934 A1 Sep. 28, 2023

Related U.S. Application Data

(63) Continuation of application No. 16/624,106, filed as application No. PCT/GB2018/051733 on Jun. 21, 2018, now abandoned.

(30) Foreign Application Priority Data

Jun. 23, 2017 (GB) ...................................... 1710042

(51) Int. Cl.
*A61K 31/05* (2006.01)
*A61P 35/00* (2006.01)
*A61K 45/06* (2006.01)

(52) U.S. Cl.
CPC .............. *A61K 31/05* (2013.01); *A61P 35/00* (2018.01); *A61K 45/06* (2013.01)

(58) Field of Classification Search
CPC .................................. C07D 31/05; A61K 31/05
See application file for complete search history.

(56) References Cited

U.S. PATENT DOCUMENTS

| | | |
|---|---|---|
| 2,304,669 A | 12/1942 | Adams |
| 6,383,513 B1 | 5/2002 | Watts et al. |
| 6,403,126 B1 | 6/2002 | Webster |
| 6,949,582 B1 | 9/2005 | Wallace |
| 7,025,992 B2 | 4/2006 | Whittle et al. |
| 8,222,292 B2 | 7/2012 | Goskonda et al. |
| 8,293,786 B2 | 10/2012 | Stinchcomb |
| 8,603,515 B2 | 12/2013 | Whittle |
| 8,632,825 B2 | 1/2014 | Velasco Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,095,555 B2 | 8/2015 | Winnicki |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,477,019 B2 | 10/2016 | Li et al. |
| 9,492,438 B2 | 11/2016 | Pollard |
| 9,522,123 B2 | 12/2016 | Whalley et al. |
| 9,630,941 B2 | 4/2017 | Elsohly et al. |
| 9,675,654 B2 | 6/2017 | Parolaro et al. |
| 9,680,796 B2 | 6/2017 | Miller et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

Zuardi et al. Frontiers in Pharmacology 2017, 8, Article 259 (Year: 2017).*

(Continued)

*Primary Examiner* — Matthew P Coughlin
(74) *Attorney, Agent, or Firm* — Cooley LLP

(57) ABSTRACT

The present invention relates to the use of cannabidiol (CBD) for the treatment of tumours associated with Tuberous Sclerosis Complex (TSC). In particular the CBD was able to decrease the number and size of marker cells, pS6, in a zebrafish model of TSC. This is suggestive of a disease modifying effect whereby treatment with CBD could result in the reduction or prevention of the benign tumours that occur in TSC patients. Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD. In use the CBD is given concomitantly with one or more other drugs used in the treatment of TSC. Such drugs may include rapamycin and/or everolimus.

22 Claims, 6 Drawing Sheets

(56) References Cited

U.S. PATENT DOCUMENTS

| | | |
|---|---|---|
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,925,525 B2 | 2/2021 | Nakaji |
| 10,966,939 B2 | 4/2021 | Guy et al. |
| 11,000,486 B2 | 5/2021 | Liu et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,224,600 B2 | 1/2022 | Vangara et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,331,279 B2 | 5/2022 | Vangara et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,709,671 B2 | 7/2023 | Joubert et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy et al. |
| 12,023,305 B2 | 7/2024 | Whalley et al. |
| 12,064,398 B2 | 8/2024 | Wright et al. |
| 12,064,399 B2 | 8/2024 | Guy et al. |
| 12,102,619 B2 | 10/2024 | Guy et al. |
| 12,121,499 B2 | 10/2024 | Whalley et al. |
| 2004/0034108 A1 | 2/2004 | Whittle |
| 2004/0049059 A1 | 3/2004 | Mueller |
| 2004/0110828 A1 | 6/2004 | Chowdhury et al. |
| 2004/0147767 A1 | 7/2004 | Whittle et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2006/0167283 A1 | 7/2006 | Flockhart et al. |
| 2007/0060638 A1 | 3/2007 | Olmstead |
| 2007/0099987 A1 | 5/2007 | Weiss et al. |
| 2007/0238786 A1 | 10/2007 | Hobden et al. |
| 2008/0112895 A1 | 5/2008 | Kottayil et al. |
| 2008/0119544 A1 | 5/2008 | Guy et al. |
| 2008/0188461 A1 | 8/2008 | Guan |
| 2009/0036523 A1 | 2/2009 | Stinchcomb et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0273895 A1 | 10/2010 | Stinchcomb et al. |
| 2010/0317729 A1 | 12/2010 | Guy et al. |
| 2011/0028431 A1 | 2/2011 | Zerbe et al. |
| 2011/0033529 A1 | 2/2011 | Samantaray et al. |
| 2011/0038958 A1 | 2/2011 | Kikuchi et al. |
| 2011/0082195 A1 | 2/2011 | Guy et al. |
| 2011/0150825 A1 | 6/2011 | Buggy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister |
| 2013/0143894 A1 | 6/2013 | Bergstrom et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara et al. |
| 2015/0359755 A1 | 12/2015 | Guy et al. |
| 2015/0359756 A1 | 12/2015 | Guy et al. |
| 2016/0010126 A1 | 1/2016 | Poulos et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2016/0317468 A1 | 11/2016 | Sankar et al. |
| 2016/0338974 A1 | 11/2016 | Aung-Din |
| 2017/0007551 A1 | 1/2017 | Guy et al. |
| 2017/0008868 A1 | 1/2017 | Dialer et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0031601 A1 | 1/2019 | Elsohly et al. |
| 2019/0083418 A1 | 3/2019 | Guy et al. |
| 2019/0091171 A1 | 3/2019 | Guy et al. |
| 2019/0160393 A1 | 5/2019 | Marshall et al. |
| 2019/0167583 A1 | 6/2019 | Shah |
| 2019/0175547 A1 | 6/2019 | Stott et al. |
| 2019/0247324 A1 | 8/2019 | Whalley et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0000741 A1 | 1/2020 | Guy et al. |
| 2020/0069608 A1 | 3/2020 | Guy et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0323792 A1 | 10/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |

(56) References Cited

U.S. PATENT DOCUMENTS

| | | |
|---|---|---|
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0093581 A1 | 4/2021 | Guy et al. |
| 2021/0100755 A1 | 4/2021 | Whalley et al. |
| 2021/0145765 A1 | 5/2021 | Guy et al. |
| 2021/0169824 A1 | 6/2021 | Guy et al. |
| 2021/0177773 A1 | 6/2021 | Guy et al. |
| 2021/0196651 A1 | 7/2021 | Guy et al. |
| 2021/0230145 A1 | 7/2021 | Blankman et al. |
| 2021/0244685 A1 | 8/2021 | Guy et al. |
| 2021/0267950 A1 | 9/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0323375 A1 | 10/2022 | Guy et al. |
| 2022/0362149 A1 | 11/2022 | Shah |
| 2022/0378714 A1 | 12/2022 | Guy et al. |
| 2022/0378715 A1 | 12/2022 | Guy et al. |
| 2022/0378717 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0043388 A1 | 2/2024 | Silcock et al. |
| 2024/0050452 A1 | 2/2024 | Craig et al. |
| 2024/0091241 A1 | 4/2024 | Guy et al. |
| 2024/0130981 A1 | 4/2024 | Wilkhu et al. |
| 2024/0131041 A1 | 4/2024 | Tse et al. |
| 2024/0165048 A1 | 5/2024 | Guy et al. |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse et al. |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy |
| 2024/0293762 A1 | 9/2024 | Loft et al. |
| 2024/0350428 A1 | 10/2024 | Guy et al. |
| 2024/0360060 A1 | 10/2024 | Silcock et al. |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| DE | 10 2012 105 063 A1 | 12/2013 |
| EP | 2 448 637 B1 | 5/2012 |
| EP | 2 578 561 A1 | 4/2013 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2 485 291 A | 5/2012 |
| GB | 2471565 B | 7/2012 |
| GB | 2478072 B | 12/2012 |
| GB | 2478074 B | 12/2012 |
| GB | 2531093 A | 4/2016 |
| GB | 2531282 A | 4/2016 |
| GB | 2539472 A | 12/2016 |
| WO | WO 2002/064109 A2 | 8/2002 |
| WO | WO 2003/099302 A1 | 12/2003 |
| WO | WO 2004/016246 A1 | 2/2004 |
| WO | WO 2004/016277 A2 | 2/2004 |
| WO | WO 2004/026802 A1 | 4/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/021394 A2 | 12/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/032351 A1 | 3/2013 |
| WO | WO 2014/168131 A1 | 11/2013 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059399 A1 | 4/2016 |
| WO | WO 2016/059405 A1 | 4/2016 |
| WO | WO 2016/084075 A1 | 6/2016 |
| WO | WO 2016/118391 A1 | 7/2016 |
| WO | WO 2016/147186 A1 | 9/2016 |

(56) References Cited

FOREIGN PATENT DOCUMENTS

| WO | WO 2016/022936 A1 | 11/2016 | | |
|----|----|----|----|----|
| WO | WO 2016/191651 A1 | 12/2016 | | |
| WO | WO 2016/199148 A1 | 12/2016 | | |
| WO | WO 2017/139496 A1 | 8/2017 | | |
| WO | WO 2017/168138 A1 | 10/2017 | | |
| WO | WO 2017/204986 A1 | 11/2017 | | |
| WO | WO 2018/002636 A1 | 1/2018 | | |
| WO | WO 2018/002637 A1 | 1/2018 | | |
| WO | WO 2018/002665 A1 | 1/2018 | | |
| WO | WO 2018/037203 A1 | 3/2018 | | |
| WO | WO-2018234811 A1 | * 12/2018 | ............. | A61K 31/05 |
| WO | WO 2019/020738 A1 | 1/2019 | | |
| WO | WO 2019/145700 A1 | 8/2019 | | |
| WO | WO 2020/225540 A1 | 11/2020 | | |
| WO | WO 2021/019231 A1 | 2/2021 | | |

OTHER PUBLICATIONS

Kobayashi et al. Cancer Research 1999, 59, 1206-1211 (Year: 1999).*

Serra et al. Behavioural Brain Research 2019, 363, 135-144 (Year: 2019).*

U.S. Appl. No. 61/969,070, filed Mar. 21, 2014, Kane et al.

U.S. Appl. No. 62/004,495, filed May 29, 2014, Vangara et al.

U.S. Appl. No. 62/154,660, filed Apr. 29, 2015, Vangara et al.

U.S. Appl. No. 14/724,351, filed May 28, 2015, Vangara et al.

Adams, R. et al., "Isolation of Cannabinol, Cannabidiol and Quebrachitol from Red Oil of Minnesota Wild Hemp," J. Am. Chem. Soc. 1940, 62, 8, 2194-2196.

Afinitor® (everolimus) tablets, for oral use, and Afinitor Disperz® (everolimus tablets for oral suspension) Prescribing Information, 2009, 49 pages.

Akiyama, M. et al., "Dravet Syndrome:A Genetic Epileptic Disorder," Acta. Med. Okayama, 66(5):369-376 (2012).

Allen G., "Florida Bill Would Allow Medical Marijuana for Child Seizures," Jan. 16, 2014, retrieved from https://www.npr.org/sections/health-shots/2014/01/16/262481852/florida-bill-would-allow-marijuana-extract-for-child-seizures, 16 pages.

[Anonymous], "GW Pharmaceuticals Announces Epidiolex Receives Fast Track Designation from FDA for the Treatment of Dravet Syndrome," GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.

[Anonymous], "GW Pharmaceuticals Receives Orphan Drug Designation by FDA for Epidiolex® in the Treatment of Lennox-Gastaut Syndrome," GW Pharmaceuticals Press Release, Feb. 28, 2014; https://www.gwpharm.com/ir/press-releases/gw-pharmaceuticals-receives-orphan-drug-designation-fda-epidiolexr-treatment, 4 pages.

Approval Letter for NDA 210365 Epidiolex, Jun. 25, 2018, 12 pages.

Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.

[No Author Listed] "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release dated Nov. 14, 2013, 3 pages.

[No Author Listed] GW Pharmaceuticals Provides Update on Orphan Program in Childhood Epilepsy for Epidiolex, GW. Pharm. Available online Nov. 14, 2013, Retrieved Feb. 10, 2017, 5 pages.

[No Author Listed] "What are the Highest CBD Strains?" accessed Feb. 16, 2017, published Oct. 15, 2014, 2 pages.

[No Author Listed] "Cannabidiol Therapy for Aicardi Syndrome" Aug. 2014, 4 pages.

[Author Unknown], Cannabinoid. Wikipedia. Retrieved on Jul. 9, 2015 from https://en.wikipedia.org/wiki/Cannabinoid, 15 pages.

[No Author Listed] "Convulsive Disorders and Their Interference with Driving," Medicos., Retrieved Feb. 10, 2017, Retrieved from internet: URL https://www.medicosporlaseguridadvial.com/en/clinical-subjects/neurologic-diseases/convulsive- disorders-and-their-interference-with-driving/, 2014, 3 pages.

[No Author Listed] "Estimating the Maximum Safe Starting Dose in Initial Clinical Trials for Therapeutics in Adult Healthy Volunteers," FDA Guidance for Industry, Jul. 2005, 30 pages.

[No Author Listed] "GW Pharmaceuticals Announces Physician Reports of Epidiolex Treatment Effect in Children and Young Adults with Treatment-resistant epilepsy from Physician-Led Expanded Access Treatment Program," GW Pharmaceuticals Press Release dated Jun. 17, 2014, 2 pages.

[No Author Listed], Cover and Table of Contents, J Pharmacology and Exp Therapeutics, Feb. 2010, 332(2), 4 pages.

[No Author Listed], "Missouri House passes cannabis extract legislation," Kansas City Star, 2014, https://kansascity.com/news/politics-government/article346747.html, 2 pages.

[No Author Listed], "High Rollers Bet On Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.

[No Author Listed], "Selected Media Examples of Pediatric Applications ofCannabidiol (CBD)," Jun. 30, 2013, 4 pages; https://www.420magazine.com/community/threads/selected-media-examples-of-pediatric-applications-of-cannabidiol-cbd.192155/.

Alger, B. E., "Not too excited? Thank your endocannabinoids," Neuron, 51(4):393-595 (2006).

Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.

American Epilepsy Society, Three Studies Shed New Light on the Effectiveness of Cannabis in Epilepsy, Oct. 14, 2014, 2 pages.

Ames, F. R. et al., "Anticonvulsant effect of cannabidiol," S Afr Med J. Jan. 4, 1986; 69(1):14, 1 page.

Annex to the Communication—Opposition for Application No. 10734541.5, dated Jan. 28, 2016, 5 pages.

Arain, A. M., "Pregabalin in the management of partial epilepsy," Neuropsychiatr Dis Treat., 407-13 (2009); Epub Aug. 20, 2009.

Arslan, A. & Tirnaksiz, F., "Self-emulsifying Drug Delivery Systems," F Abad J Pharm Sci, 38(1):55-64 (2013).

Arzimanoglou et al., "All children who experience epileptic falls do not necessarily have Lennox-Gastaut syndrome . . . but many do," Epileptic Disord. 2011, 13: S3-S13 (2011).

Avoli, M. et al., "Cellular and molecular mechanisms of epilepsy in the human brain," Prog Neurobiol., 77(3):166-200 (2005).

Bakhsh, K., "Pregabalin in the management of partial epilepsy," Miftaah-al-Khazaain, 1930:607-608, with English translation, 4 pages.

Bancaud, et al., "Proposal for Revised Clinical and Electroencephalographic Classification of Epileptic Seizures," Epilepsia, 22(4):489-501 (1981).

Banerjee et al., "Case Report: Aicardi syndrome: A report of five Indian cases," Neurology India, 54(1):91-93 (2006).

Barker-Haliski, M. et al., "How Clinical Development Can, and Should Inform Translational Science," Neuron, 84:582-593 (2014).

Bell, J., "Treatment With CBD In Oily Solution of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.

Benowitz, N. L. et al., "Metabolic and Psychophysiologic studies of cannabidiol hexobarbital interaction," Clin Pharmacol Ther., 28(1):115-120 (1980).

Bergamaschi, M. M. et al., "Safety and Side Effects of Cannabidiol, a Cannabis sativa Constituent," Current Drug Safety, 6:237-249 (2011).

Bertram, E., "The Relevance of Kindling for Human Epilepsy," Epilepsia, 48(Suppl. 2):65-74 (2007).

(56) References Cited

OTHER PUBLICATIONS

Bipolar Health Group (Charlotte's Web Hemp Remedy, available online at http:/bipolarhealthgroup.org/index.php/charlottes-web-hemp-remedy/, accessed Sep. 6, 2017, 6 pages.
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, S. et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009 .17.
Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.
Bijnsdorp, I. V. et al., "Analysis of Drug Interactions," Chapter 34, Cancer Cell Culture, Methods in Molecular Biology, Second Edition, lan A. Cree, Ed., 2011:731:421-34, 19 pages.
Bostanci, M. O. & Bagirici, F., "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brown et al., Child Neurology Foundation, "LGS" (Lennox-Gastaut Syndrome), available at http://www.childneurologyfoundation.org/disorders/lgs-lennox-gastaut-syndrome, 2019, 7 pages.
Brust, J. C. M. et al., "Marijuana use and the risk of new onset seizures," Trans Am Clin Climatol Assoc., 103:176-181 (1992).
Gardner, "Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.
Camfield, "Definition and natural history of Lennox-Gastaut Syndrome," Epilepsia, 52:3-9 (2011).
Capal, J. K. & Franz, D. N., "Profile of everolimus in the treatment of tuberous sclerosis complex: an evidence-based review of its place in therapy," Neuropsychiatric Disease and Treatment, 12:2165-2172 (2016).
Carlini, et al., "Hypnotic and antiepileptic effects of cannabidiol," J Clin Pharmacol. Aug.-Sep. 1981-21(8-9 Suppl):417S-427S. Medline abstract only.
Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.
Carvill, G. L. et al., "GABRA1 and STXBP1: Novel generic causes of Dravet Syndrome," Neurology, 82:1245-1253 (2014).
Castel-Branco, et al., "The Maximal Electroshock Seizure (MES) Model in the Preclinical 98. Assessment of Potential New Anti epileptic Drugs," Methods Find Exp Clin Pharmacol., 31(2): 101-106 (2009).
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.
Charlotte's Web [online], "When to expect Results from CW Hemp Oil," Mar. 13, 2017, retrieved on May 21, 2018, URL https://www.cwhemp.com/blog/expecting-results-from-hemp, 6 pages.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennon-gastaut-syndrome, 10 pages.

Chiron, C. & Dulac, O., "The Pharmacologic Treatment of Dravet Syndrome," Epilepsia, 52 (Suppl. 2):72-75 (2011).
Chiron, S., "Stiripentol for the treatment of Dravet syndrome," Orphan Drugs: Research and Reviews, 4:29-38 (2014).
Chiu, P. et al., "The Influence of Cannabidiol and Δ-Tetrahydro-cannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev, 58(3):621-681 (2006).
Chou, T.-C., "Drug Combination Studies and Their Synergy Quantification Using the Chou-Talalay Method," Cancer Res, 70(2):440-446 (2010).
Christians, U. et al., "Biomarkers of Immunosuppressant Organ Toxicity after Transplantation—Status, Concepts and Misconceptions," Expert Opin Drug Metab Toxicol., 7(2): 175-200 (2011).
Chu-Shore, C. J. et al., "The natural history of epilepsy in tuberous sclerosis complex," Epilepsia, 51(7):1236-1241, 2010; doi: 10.1111/j.1528-1167.2009.02474.
Cilio, M. R. et al., "The case for assessing cannabidiol I epilepsy," Epilepsia, 55(6):787-790 (2014).
clinical trials.gov [online], Identifier: NCT02224690, A Study to Investigate the Efficacy and Safety of Cannabidiol (GWP42003-P; CBD) as Adjunctive Treatment for Seizures Associated With Lennox-Gastaut Syndrome in Children and Adults (GWPCARE4) Jazz Pharmaceuticals, U.S. National Library of Medicine, last update posted Sep. 8, 2022, 3 pages; Retrieved from https://clinicaltrials.gov/ct2/show/NCT02224690.
clinical trials.gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.
clinical trials.gov [online], Identifier: NCT02006628, A study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
clinical trials.gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
clinical trials.gov [online], Identifier: NCT02544750, "An open-label Extension Trial of Cannabidiol (GWP42003-P, Cbd) for Seizures in Tuberous Sclerosis Complex (GWPCARE6)," Sponsor: GW Research Ltd, U.S. National Library of Medicine, Oct. 1, 2018; Retrieved from https://clinicaltrials.gov/ct2/show/NCT02544750, 6 pages.
Clinical Drug Interaction Studies—Cytochrome P450 Enzyme- and Transporter-Mediated Drug Interactions Guidance for Industry, U.S. Department of Health and Human Services, Food and Drug Administration, Center for Drug Evaluation and Research (CDER), Jan. 2020, 27 pages.
Collins, T. R., What Neurologists are Doing About Medical Marijuana?, Neurology Today, Apr. 17, 2014, vol. 4, issue 8, 8 pages.
Combined Search and Examination Report mailed Jan. 4, 2012 for Application No. GB 1116789.7, 8 pages.
Combined Search and Examination Report mailed Mar. 25, 2011 for Application No. GB 1100043.7, 8 pages.
Combined Search and Examination Report mailed Sep. 5, 2014 for Application No. GB 1414813 .4, 8 pages.
Combined Search and Examination Report Under Sections 17 and 18 (3) for International Application No. GB1121919.3, dated Feb. 29, 2012, 8 pages.
Combined Search and Examination Report Under Sections 17 and 18 (3) for International Application No. GB 141077 I .8, dated Feb. 27, 2018, 7 pages.

(56) References Cited

OTHER PUBLICATIONS

Combined Search and Examination Report Under Sections 17 and 18 (3) for International Application No. GB 1418166.3, dated Jul. 2, 2015, 8 pages.
Combined Search and Examination Report Under Sections 17 and 18 (3) for International Application No. GB 1418170.5, dated Jul. 2, 2015, 6 pages.
Combined Search and Examination Report Under Sections 17 and 18 (3) for International Application No. GB 1418171.3, dated Jun. 29, 2015, 8 pages.
Combined Search and Examination Report Under Sections 17 and 18 (3) for International Application No. GB 1506550.1, dated Feb. 5, 2016, 9 pages.
Communication of a Notice of Opposition for Application No. 107342541.5 dated Dec. 17, 2014, 1 page.
Communication Pursuant to Article 94(3) EPC in European Patent Application No. 10734541.5, dated Oct. 23, 2012, 1 page.
Conry, J. A. et al., "Clobazam in the treatment of Lennox-Gastaut syndrome," Epilepsia, 50:1158-1166 (2009).
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marihuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Controlled clinical trial of cannabidiol in Huntington's Disease," Pharmacology Biochemistry & Behavior, 40:701-708 (1991).
Consroe, et al., "Effects of cannabidiol on behavioral seizures caused by convulsant drugs or current in mice," Eur J Pharmacol., 83(3-4):293-298 (1982).
Consroe et al.,. "Therapeutic Potential of Cannabinoids in Neurological Disorders," Cannabonioids as Therapeutic Agents, R. Mechoulam, Ed., 1986, pp. 21-49.
Consroe, et al. Chapter 12, "Potential Role of Cannabinoids for Therapy of Neurological Disorders." p. 459 in Marijuana Cannabinoids: Neurobiology and Neurophysiology, ed. L. Murphy (1992), 72 pages.
Consroe et al., "Open label evaluation of cannabidiol in dystonic movement disorders," International Journal of Neuroscience, 30(4):277-282 (1986); doi: 10.3109/00207458608985678.
Cortesi, et al., "Potential therapeutical effects of cannabidiol in children with pharmacoresistant epilepsy," Med Hypotheses, 68(4):920-921 2007). Epub Nov. 16, 2006.
Cortez, et al. Chapter 10, "Pharmacologic Models of Generalized Absence Seizures in Rodents," Models of Seizures and Epilepsy, 111-126 (2006).
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Crespel, A. et al., "Lennox-Gastaut Syndrome," Chapter 14, in Epileptic Syndromes in Infancy, Childhood, and Adolescence, 5th Edition, ed. M. Bureau, et al., pp. 189-216 (2012).
Crumrine, P. K., "Management of Seizures in Lennox-Gastaut Syndrome," Pediatr Drugs, 13(2):107-118 (2011).
Cunha, et al., "Chronic administration of cannabidiol to healthy volunteers and epileptic patients," Pharmacology, 21(3):175-85 (1980).

Curatolo, P. et al., "Management of epilepsy associated with tuberous sclerosis complex (TSC): Clinical recommendations," European Journal of Paediatric Neurology, 16:582-586 (2012).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures, " J Neurolog Sci., 150:S162 (1997), 2 pages.
Dasa, et al. "Brhat Nighantu Ratnakara (Saligramanighantubhusanam)." vol. IV. 1997:170. Sanskrit. Exhibit 5, 5 pages.
Davis, et al., "A predominant role for inhibition of the adenylate cyclase/protein kinase. A pathway in ERK activation by cannabinoid receptor 1 in NIE-115 neuroblastoma cells," J Biol Chem., 278(49): 48973-80 (2003). Epub Sep. 29, 2003.
Davis, et al., "Antiepileptic action of marijuana-active substances," Federation Proceedings, 8:284-5 (1949).
Decision in IPR2017 -00503 dated Jul. 7, 2017, 26 pages.
Decision in Opposition proceedings (Art. 101(3)(a) and 106(2) EPC in European Patent Application No. EP2448637, dated Dec. 15, 2016, 91 pages.
Depakene (valproic acid) capsules and oral solution, CV, Prescribing Information, 1978, 54 pages; https://www.accessdata.fda.gov/drugsatfda_docs/label/2013/018081s056lbl.pdf.
De Oliveira, et al., "Anticonvulsant activity of β-caryophyllene against pentylenetetrazol-induced seizures," Epilepsy Behav., 56:26-31 (2016); doi: 10.1016/j.yebeh.2015.12.040.
Devinsky, et al., "Cannabidiol: Pharmacology and potential therapeutic role in epilepsy and other neuropsychiatric disorders," Epilepsia, 55(6):791-802 (2014).
Diacomit™ Product Monograph, Submission Control 142417, Date of Preparation, Dec. 19, 2012, 37 pages.
Dilantin-125®, NDA 08762 Dilantin-125 (Phenytoin Oral Suspension, USP) FDA Approved Labeling Text dated Feb. 2013, 15 pages.
DiMarzo, V., Declaration Under 37 C.F.R. 1.132, dated Aug. 24, 2017, 21 pages.
Dravet, "The core Dravet syndrome phenotype," Epilepsia, 52 Suppl 2:3-9 (2011); doi: 10.1111/j.1528-1167.2011.02994.x.
Dreifus, et al., "Proposal for Revised Clinical and Electroencephalographic Classification of Epileptic Seizures," Epilepsie., 22:489-501 (1981).
Moral, M. A. et al., "Pipeline on the Move," Drugs of the Future, 39(1): 49-56, Jan. 2014.
Dulac, "Use of Lamotrigine in Lennox-Gastaut and Related Epilepsy Syndromes," J. Child Neurolog., 12(Supplement 1): S23-S29 (1997).
Dulac, "Vigabatrin in Childhood Epilepsy," J. Child Neurolog., 6(Supplement 2): S30-S37 (1991).
Eadie, "Shortcomings in the current treatment of epilepsy," Expert Rev Neurother., 12(12):1419-27 (2012).
Ebrahimi-Fakhari, D. et al., "Cannabidiol Elevates mTOR Inhibitor Levels In Tuberous Sclerosis Complex Patients," (2020) Pediatric Neurology, 12 pages; https://doi.org/10.1016/j.pediatrneurol.2019.11.017.
Engel, "Report of the ILAE classification core group," Epilepsia, 47(9):1558-68 (2006).
Engel, "What should be modeled," in Models Seizure Epilepsy, 2006, 14 pages.
Eggers, "Temporal lobe epilepsy is a disease of faulty neuronal resonators rather than oscillators, and all seizures are provoked, usually by stress," Med Hypotheses.,69(6):1284-9 (2007).
Epilepsy Patients Flock to Colorado after Medical Pot Gives Them Hope, Nov. 18, 2013, CBS Colorado News, 4 pages.
Elsohly and Gul, "Constituents of Cannabis Sativa," Chapter 1, Handbook of Cannabis, Roger G. Pertwee, Ed., pp. 3-22 (2014).
Elsohly, M. & Gul, W., "Chemical constituents of marijuana: The complex mixture of natural cannabinoids," Life Sciences, 78:539-548 (2005).
Epidiolex® (cannabidiol) oral solution, CV, Prescribing Information, 2018, 30 pages; https://www.accessdata.fda.gov/drugsatfda_docs/label/2018/210365lbl.pdf.
Ettienne De Meijer, "The Chemical Phenotypes (Chemotypes) of Cannabis," Chapter 5, Handbook of Cannabis, Handbook of Cannabis, Roger G. Pertwee (ed.), pp. 89-110 (2014).

(56) References Cited

OTHER PUBLICATIONS

Ex parte Edelstam, Appeal No. 2016/006358, mail date Jun. 21, 2017 (Year: 2017), 5 pages.
Ex parte Miller, Appeal 2009-011751, mail date Jul. 8, 2010 (Year: 2010), 23 pages.
Examination Report mailed Mar. 18, 2014 for Application No. GB1100043.7, 3 pages.
Expert Statement of Vincenzo Di Marzo for Application No. EP10734541.5 dated Sep. 9, 2016, 10 pages.
Expert Statement of Professor Benjamin J. Whalley for Application No. EP10734541.5 dated Sep. 9, 2016, 11 pages.
Expert Statement of Professor Anthony G. Marson for Application No. EP10734541.5, 10 pages.
Expert Statement of Dr. Emma Louise Cheetham in European Application No. EP10743541.5, dated Nov. 4, 2016, 6 pages.
FDA, "Warning Letters and Test Results for Cannabidiol-Related Products," 2016 Warning Letters, 4 pages.
FDA, "Warning Letters and Test Results for Cannabidiol-Related Products," 2015 Warning Letters, 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
FDA'S Guidance for Industry Q3A Impurities in New Drug Substances, Revision 2, Jun. 2008, 17 pages.
FDA Guideline for Submitting Supporting Documentation in Drug Applications for the Manufacture of Drug Substances, published in 1987, 20 pages.
Fariello, "Parenteral Penicillin in Rats: An Experimental Model of Multifocal Epilepsy," Epilepsia, 17:217-222 (1976).
Ferdinand, et al., "Cannabis—psychosis pathway independent of other types of psychopathology," Schizophr Res., 79(2-3):289-295 (2005).
Fernandez-Ruiz, J. et al., "Cannabidiol for neurodegenerative disorders: important new clinical applications for this phytocannabinoid?" British Journal of Pharmacology, 75(2):323-333 (2012).
Fisher, et al., "The impact of epilepsy from the patient's perspective I. Descriptions and subjective perceptions," Epilepsy Res.,41(1):39-51 (2000).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>, 22 pages.
French, J. A. et al., "Adjunctive everolimus therapy for treatment-resistant focal-onset seizures associated with tuberous sclerosis (EXIST-3): a phase 3, randomised, double-blind, placebo-controlled study," Lancet, 388:2153-2163 (2016).
Gabor, et al., "Lorazepam versus phenobarbital: Candidates for drug of choice for treatment of status epilepticus," J Epilepsy, 3(1):3-6 (1990).
Gallily, et al., "Overcoming the Bell-Shaped Dose-Response of Cannabidiol by Using Cannabis Extract Enriched in Cannabidiol," Pharmacology & Pharmacy, 6:75-85 (2015).
Gaoni, Y. & Mechoulam, R., "The Isolation and Structure of Δ1-Tetrahydrocannabinol and Other Neutral Cannabinoids from Hashish," J Am Chem Soc. Jan. 13, 1971;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "GW Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Gastaut, "Clinical and electroencephalographical classification of epileptic seizures," Epilepsia, 10: Suppl:2-13 (1969).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gedde, Retrospective Case Review of High CBD, Low THC Cannabis Extract (Realm Oil) for Intractable Seizure Disorders, 2013 Realm of Caring Foundation, 4 pages.
Gedde, "Clinical Experience with Cannabis in Treatment-Resistant Pediatric Epilepsy," http://www.theroc.us/images/gedde presentation.pdf, Sep. 9-11, 2014, 45 pages.
Gedde et al., "Whole Cannabis Extract of High Concentration Cannabidiol May Calm Seizures in Highly Refractory Pediatric Epilepsies," American Epilepsy Society, Dec. 2013, pp. 449-1450. Abstract.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Gemmill, R. M. et al., "Synergistic growth inhibition by Iressa and Rapaymycin is modulated by VHL mutations in renal cell carcinoma," British Journal of Cancer, 92:2266-2277 (2005).
Gloss, D. & Vickrey, B., "Cannabinoids for epilepsy (Review)," Cochrane Database of Systematic Reviews 2014, Issue 3. Art. No. CD009270, 9 pages; DOI: 10.1002/14651858.CD009270.pub3.
Green, "CBD: An Unconventional Therapy," available online at http://nugs.com/article/cbd-an¬unconventional-therapy.html, published Mar. 24, 2014, 5 pages.
Gresham, et al., "Treating Lennox-Gastaut syndrome in epileptic pediatric patients with third generation rufinamide," Neuropsychiatr Dis Treat., 6:639-645 (2010).
Gross, et al., "Marijuana use and epilepsy: prevalence in patients of a tertiary care epilepsy center," Neurology, 62(11):2095-7 (2004).
Grotenhermen et al., "The Therapeutic Potential of Cannabis and Cannabinoids," Dtsch Arztebl Int, 109(29-30): 495-501 (2012); doi:10.3238/arztebl.2012.0495.
Guerrini, et al., "Lamotrigine and Seizure Aggravation in Severe Myoclonic Epilepsy," Epilepsia, 39(5):508-512 (1998).
Guimares, et al., "Antianxiety effect of cannabidiol in the elevated plus-maze," Psychopharmacology (Berl)., 100(4):558-9 (1990); doi: 10.1007/BF02244012.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, 8 pages.
GWPharm [online], "GW Pharmaceuticals Provides Update on Orphan Program in Childhood Epilepsy for Epidiolex®," GW Pharmaceuticals Press Release, Nov. 15, 2013, 5 pages.
Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.
Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.
Hauser, N. et al., "High on Cannabis and Calcineurin Inhibitors: A Word of Warning in an Era of Legalized Marijuana," Hindawi

(56) References Cited

OTHER PUBLICATIONS

Publishing Corporation, Case Reports in Transplantation, vol. 2016, Sep. 6, 2018;2018:7095846. doi: 10.1155/2018/7095846. eCollection 2018, 4 pages.

Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J_tot_lament_medical_marijuana_delays.html.

Hegde, M. et al., "Seizure exacerbation in two patients with focal epilepsy following marijuana cessation," Epilepsy & Behavior, 25:563-566 (2012).

Heinemann, et al., "An Overview of in Vitro Seizure Models in Acute and Organotypic Slices," Chapter 4, 35-44 (2006).

Herlopian, A. et al., "Cannabidiol in treatment of refractory epileptic spasms: An open label study," Epilepsy & Behavior, 106:106988 (2020), 7 pages; https://doi.org/10.1016/j.yebeh.2020.106988.

Hess et al., "Cannabidiol as a new treatment for drug-resistant epilepsy in tuberous sclerosis complex," Epilepsia, 57(10):1617-1624 (2016).

Hill, et al., "α9-Tetrahydrocannabivarin suppresses in vitro epileptiform and in vivo seizure activity in adult rats." Epilepsia, 51(8):1522-32 (2010); doi: 10.1111/j.1528-1167.2010.02523.x. Epub Feb. 26, 2010.

Hill, "Cannabidivarin-rich cannabis extracts are anticonvulsant in mouse and rat via a CB 1 receptor-independent mechanism," British Journal of Pharmacology, 170(3):679-692 (2013).

Hill et al., "Cannabidivarin is anticonvulsant in mouse and rat," Br. J Pharmacol, 167(8): 1629-1642 (2012).

Hill, A. J. et al., "Phytocannabinoids as novel therapeutic agents in CNS disorders," Pharmacology & Therapeutics, 133:79-97 (2012).

Hillig, K. W. & Mahlberg, P. G., "A chemotaxonomic analysis of cannabinoid variation in *Cannabis* (Cannabaceae)," American Journal of Botany, 91(6):966-975 (2004).

Holmes, et al., "Choosing the correct AED: From Animal Studies to the Clinic," Pediatr Neurol. 38(3):151-162 (2008).

Holmes, G. L. et al., "Tuberous Sclerosis Complex and Epilepsy: Recent Developments and Future Challenges," Epilepsia, 48(4):617-630, 2007.

Iannotti, et al., "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-41 (2014); doi: 10.1021/cn5000524.

ICE Epilepsy Alliance, The Dravet Syndrome Spectrum, Nov. 2008, 2 pages.

*Insys Development Company, Inc. v. GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.

*Insys Development Company, Inc. v. GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.

*Insys Development Company, Inc. v. GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.

*Insys Development Company, Inc. v. GW Pharma Limited and Otsuka Pharmaceutical Co., Ltd.*, Final Written Decision in IPR2017-00503, U.S. Pat. No. 9,066,920, dated Jan. 3, 2019, 40 pages.

International Preliminary Report on Patentability in International Application No. PCT/GB2010/051066, dated May 3, 2011, 4 pages.

International Preliminary Report on Patentability for International Application No. PCT/GB2017/052229, dated Feb. 26, 2019, 7 pages.

International Preliminary Report on Patentability for International Application No. PCT/GB2017/052229, dated Oct. 6, 2017, 10 pages.

International Search Report and Written Opinion for International Application No. PCT/GB2017/051913, dated Sep. 15, 2017, 9 pages.

International Search Report and Written Opinion for International Application No. PCT/GB2017/051914, dated Sep. 12, 2017, 10 pages.

International Preliminary Report on Patentability mailed Dec. 12, 2013 for International Application No. PCT/GB2012/052284, 12 pages.

International Search Report and Written Opinion mailed Dec. 13, 2010 for International Application No. PCT/GB2010/051066, 3 pages.

International Search Report and Written Opinion mailed May 30, 2011 for International Application No. PCT/GB2011/050649, 15 pages.

International Search Report mailed Feb. 24, 2012 for International Application No. PCT/GB2012/050002, 10 pages.

IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.

Iuvone, et al., "Neuroprotective effect of cannabidiol, a non-psychoactive component from Cannabis sativa, on beta-amyloid-induced toxicity in PC12 cells," J Neurochem., 89(1):134-41 (2004).

Iwasaki, I., "Metabolism of Tacrolimus (FK506) and Recent Topics in Clinical Pharmacokinetics," Drug Metab. Pharmacokinet., 22(5):328-335 (2007).

Izzo, et al., "Non-psychotropic plant cannabinoids: new therapeutic opportunities from an ancient herb," Trends in Pharmacological Sciences, 30(10):515-527 (2009).

Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page. Poster.

Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with--pharmaceutical-grade-cbd/.

Jaeger, W. et al., "Inhibition of cyclosporine and tetrahydrocannabinol metabolism by cannabidiol in mouse and human microsomes," Xenobiotica, 26(3):275-284 (1996).

Jeavons, et al., "Sodium valproate in treatment of epilepsy," Br Med J., 2(5919):584-6 (1974).

Jiang, R. et al., "Cannabidiol Is a Potent Inhibitor of the Catalytic Activity of Cytochrome P450 2C19," Drug Metab. Pharmacokinet., 28(4):332-338 (2013).

Jones et al. [online], Info & Metrics / Article Information," Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.

Jones et al., "Cannabidiol Displays Antiepileptiform and Antiseizure Properties in Vitro and in Vivo," J Pharmacol Exp Ther., 332(2):559-577 (2010).

Jones, N. A. et al., "Cannabidiol exerts anti-convulsant effects in animal models of temporal lobe and partial seizures," Seizure, 21:344-352 (2012).

Jones, P. G. et al., "Cannabidiol," Acta Cryst., B33:3211-3214 (1977).

Joy, et al., "Marijuana and Medicine. Assessing the Science Base," National Academy Press. Washington D.C., 1999, 170 pages.

Kahan, et al., "Risk of selection bias in randomized trials," Trials, 16:405 (2015), 7 pages.

Karler, et al., "The cannabinoids as potential antiepileptics," J Clin Pharmacol, 21(8-9 Suppl):437S-447S (1981).

Kalepu, S. et al., "Oral lipid-based drug delivery systems—an overview," Acta Pharmaceutica Sinica B., 3(6):361-372 (2013).

Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.

(56) References Cited

OTHER PUBLICATIONS

Kassai et al., "Severe Myoclonic epilepsy in Infancy: A Systematic Review and a Meta-Analysis of Individual Patient Data," Epilepsia, 49(2):343-348 (2008).
Kerr, D. N. S. & Pillai, P. M., "Clobazam as adjunctive treatment in refractory epilepsy," British Medical Journal, 286:1246-1247 (1983).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Kelley, et al., "Doose syndrome (myoclonic-astatic epilepsy): 40 years of progress," Developmental Medicine & Child Neurology, 52:988-993 (2010).
Klitgaard, et al., "Electrophysiological, neurochemical and regional effects of levetiracetam in the rat pilocarpine model of temporal lobe epilepsy," Seizure, 12(2):92-100 (2003).
Klitgaard, et al., "Evidence for a unique profile of levetiracetam in rodent models of seizures and epilepsy," European Journal of Pharmacology, 353(2):191-206 (1998).
Kopka, M., "Cannabinoids in the treatment of epilepsy—an updated review," Journal of Epileptology, 2019, 27:35-42; 10.21307/jepil-2019-004.
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250.x. Epub Aug. 29, 2011.
Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j.1528-1167.2009.02397.x. Epub Nov. 3, 2009. Erratum in: Epilepsia. Sep. 2010;51(9): 1922.
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leahy, J. T. et al., "Clobazam as an adjunctive therapy in treating seizures associated with Lennox-Gastaut syndrome," Neuropsychiatric Disease and Treatment, 7:673-681 (2011).
Leino, A. et al., "Evidence of a clinically significant drug-drug interaction between cannabidiol and tacrolimus: A case report," American Journal of Transplantation, 18 (Suppl. 4): 744-745 (2018).
Leo, et al., "Cannabidiol and epilepsy: Rationale and therapeutic potential," Pharmacological Research, 107:85-92 (2017).
Leonard, B. E., "Therapeutic Uses of Cannabis," British Medical Association (BMA). Harwood Academic Publishers, UK. 1997, pp. 592.
Letter from Opponent Regarding Oral Proceedings for European Patent No. EP2448637, dated Oct. 20, 2016, 6 pages.
Lewis, "Mystery Mechanisms," The Scientist.com, Jul. 29, 2016, retrieved on Nov. 8, 2017, 2 pages.
Lieu, et al., "Assessment of self-selection bias in a pediatric unilateral hearing loss study," Otolaryngol Head Neck Surg., 142(3):427-433 (2010).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-78 (2011); doi:10.1111/j.1528-1167.2011.03024.x.
Loscher, W. & Rogawski, M. A., "How theories evolved concerning the mechanism of action of barbiturates," Epilepsia, 53(Suppl. 8):12-25, 2012; doi: 10.1111/epi.12025.
Lutz, "On-demand activation of the endocannabinoid system in the control of neuronal excitability and epileptiform seizures," Biochem Pharmacol., 68(9):1691-8 (2004).
Lowenstein, "Chapter 363: Seizures and Epilepsy," Diseases of the Central Nervous System, 2498-2512 (2008).
Luttjohann, et al., "A revised Racine's scale for PTZ-induced seizures in rats," Physiol Behav., 98(5):579-86 (2009); doi: 10.1016/j.physbeh.2009.09.005.
Maa et al., "The case for medical marijuana in epilepsy," Epilepsia, 55(6):783-786 (2014).
Marks, W. J. et al., "Management of Seizures and Epilepsy," Am Fam Physician. 1998;57(7):1589-1600.
Mackie, "Cannabinoid receptors as therapeutic targets," Annu Rev Pharmacol Toxicol., 46:101-22 (2006).
Majoosi, et al. Kaamil-al-Sena'ah, Part II, Central Council for Research in Unani Medicine. 2005: 116. Arabic. Exhibit 2, 2 pages.
Malfait, et al. "The nonpsychoactive cannabis constituent cannabidiol is an oral anti-arthritic therapeutic in murine collagen-induced arthritis," PNAS, 97(17):9561-9566 (2000).
Manni et al., "Obstructive Sleep Apnea in a Clinical Series of Adult Epilepsy Patients: Frequency and Features of the Comorbidity," Epilepsia, 44(6):836-840 (2003).
Manno, "Status Epilepticus: Current Treatment Strategies," The Neurohospitalist, 1(1):23-31 (2011).
Masangkay, E. G., "FDA Confirms GW Pharmaceuticals' IND For Epidiolex Trial In Dravet Syndrome," May 9, 2014, 2 pages.
Mattson, et al., "Comparison of carbamazepine, phenobarbital, phenytoin, and primidone in partial and secondarily generalized tonic-clonic seizures," N. Engl. J. Med, 313(3):145-151 (1985).
Mattson, et al., "Prognosis for total control of complex partial and secondary generalized tonic clonic seizures," Neurology, 47:68-76 (1996).
Mares et al., "Electrical Stimulation-Induced Models of Seizures in Model of Seizures and Epilepsy Asla Pitkanen," Philip A. Schwartzkroin & Solomon L. Moshe, eds., 2006, 7 pages.
Martin et al., "Structure-Anticonvulsant Activity Relationships of Cannabidiol Analogs," National Institute on Drug Abuse, Research Monograph Series, 79:48-58 (1987).
McCormick et al., "On the cellular and network bases of epileptic seizures," Annu Rev Physiol., 63:815-46 (2001).
McNamara, "Chapter 19: Pharmacotherapy of the Epilepsies,", Goodman & Gilman's the Pharmacological Basis of Therapeutics 11th ed., McGraw-Hill Companies, pp. 501-525 (2006).
Mechoulam, et al., "Cannabidiol: An Overview of Some Pharmacological Aspects," J Clin Pharmacol, 42:11S-19S (2002).
Mechoulam, et al., "Toward drugs derived from cannabis," Naturwissenschaften, 65(4):174-9 (1978).
Mechoulam, R. et al., "Cannabidiol—Recent Advances," Chemistry & Biodiversity, vol. 4, pp. 1678-1692 (2007).
Mechoulam, R., "Conversation with Ralph Mechoulam," Addiction Jun. 2007;102(6):887-93. doi: 10.1111/j.1360-0443.2007.01795.x.
Mechoulam, R. & Parker, L. A., "The Endocannabinoid System and the Brain," Annu. Rev. Psychol. 2013. 64:21-47.
Mechoulam, R. & Parker, L. A., "Towards a better cannabis drug," British Journal of Pharmacology (2013) 170 1363-1364.
Mechoulam et al., "Cannabidiol: an overview of some chemical and pharmacological aspects. Part I: chemical aspects," Chemistry and Physics of Lipids, 121:35-43 (2002).
Merlis, "Proposal for an international classification of the epilepsies," Epilepsia, 1(1):114-9 (1970).

(56) References Cited

OTHER PUBLICATIONS

Miller, et al., "Mapping genetic modifiers of survival in a mouse model of Dravet syndrome," Genes, Brain and Behavior, 13:163-172 (2014).
Montenegro et al., "Efficacy of Clobazam as Add-on Therapy for Refractory Epilepsy: Experience at a US Epilepsy Center," Clinical Neuropharmacology, 31(6):333-338 (2008).
Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
Morard, et al., "Conversion to Sirolimus-Based Immunosuppression in Maintenance Liver Transplantation Patients," Liver Transplantation, 13:658-664 (2007).
Moral, et al., "Pipeline on the Move," Drugs of the Future, 39(1):49-56 (2014).
Morelli et al., "The effects of cannabidiol and its synergism with bortezomib in multiple myeloma cell lines. A role for transient receptor potential Vanilloid type-2," Blood, 110(9):3281-3290 (2014).
MyVirtualMedicalCentre [online], "Aicardi syndrome," mymc.com, Feb. 2004, retrieved on Jan. 25, 2019 at https://www.myvmc.com/diseases/aicardi-syndrome/, 6 pages.
Nabissi et al., "Cannabinoids synergize with carfilzomib, reducing multiple myeloma cells viability and migration," Oncotarget, 7:77553 (2016), 15 pages.
Nair et al., "A simple practice guide for dose conversion between animals and human," Journal of Basic and Clinical Pharmacy, 7:27-31 (2016).
Ng et al., "Illicit drug use and the risk of new-onset seizures." Am J Epidemiol., 132(1):47-57 (1990).
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
New Drug Application No. 210365 for Epidiolex (cannabidiol) 100 mg/ml oral solution, Jun. 25, 2018, 12 pages.
[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWN0OL01D20140606.
[No Author Listed], "Medical Cannabis Community Wants to Remain Apart," Medical Marijuana News, Apr. 3, 2013, 3 pages; Kitsap Peninsula Business Journal, available at: https://www.420magazine.com/community/threads/medical-cannabis-community-wants-to-remain-apart.186955/.
[No Author Listed], "Medical Marijuana for N.J. Children? It's All in Gov. Christie's Hands," CBS News New York, Jun. 27, 2013, 3 pages; https://www.cbsnews.com/newyork/news/medical-marijuana-for-n-j-children-its-all-in-gov-christies-hands/.
Notice of Allowance in U.S. Appl. No. 13/380,305, mailed Dec. 10, 2014, 5 pages.
Notice of Allowance in U.S. Appl. No. 13/380,305, mailed Mar. 19, 2015, 7 pages.
Notice of Appeal in European Patent No. EP2448637, dated Feb. 14, 2017, 5 pages.
Notice of Opposition to a European Patent No. EP2448637, Dated Dec. 5, 2014, 20 pages.
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
Office Action in U.S. Appl. No. 13/380,305, dated Aug. 25, 2014, 6 pages.
Onfi™ (clobazam) tablets Prescribing Information, NDA 202067 Onfi (clobazam) Tablets for oral use FDA Approved Labeling Text, dated Oct. 21, 2011, 28 pages.
Oguni, H. et al., "Long-Term Prognosis of Lennox-Gastaut Syndrome," Epilepsia, 37(Suppl 3):44-47 (1996).
Oguni, H. et al., "Severe myoclonic epilepsy in infants—a review based on the Tokyo women's Medical University series of 84 cases," Brain Dev., 23:736-748 (2010).
Olyaei, A. J. et al., "Interaction Between Tacrolimus and Nefazodone in a Stable Renal Transplant Recipient," Pharmacotherapy, 18(6):1356-1359 (1998).
Opponent Response to the Preliminary Opinion of the Opposition Division in European Patent No. EP2448637, dated Jun. 23, 2016, 25 pages.
Opponent Response dated to September the 9, Preliminary 2016, 25 Opinion pages of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3 pages.
Opponent Response to the Written Submissions in European Patent No. EP2448637, dated Nov. 4, 2016, 3 pages.
Palmer, A. C. et al., "Combination Cancer Therapy Can Confer Benefit via Patient-to-Patient Variability without Drug Additivity or Synergy," Cell, 171:1678-1691 (2017).
Panikasiwill, D. et al., "An endogenous cannabinoid (2-AG) is neuroprotective after brain injury," Nature 413:527-531 (2001).
Patent Owners' Preliminary Response for IPR2017-00503 dated Apr. 11, 2017, 1 page.
Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf, 2 pages.
Pellicia, et al., International Association for Cannabis as Medicine, IACM 3rd Conference on Cannabinoids in Medicine, Sep. 9-10, 2005, 2005 Conference on Cannabinoids in Medicine, 72 pages.
Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.
Pertwee, "Cannabinoid receptor ligands: clinical and neuropharmacological considerations, relevant to future drug discovery and development," Expert Opin Investig Drugs, 9(7):1553-71 (2000).
Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol., 153(2):199-215 (2008).
Pertwee, "The Pharmacology and Therapeutic Potential of Cannabidiol," Cannabinoids, Chapter 3, DiMarzo, V. (Ed.), pp. 32-83 (2004).
Petition for Inter Partes Review U.S. Pat. No. 9,066,920 dates Dec. 16, 2016, 78 pages.
Petrocellis, et al., "Effects of cannabinoids and cannabinoid-enriched Cannabis extracts on TRP channels and endocannabinoid metabolic enzymes," British Journal of Pharmacology, 163: 1479-1494 (2011).
Pohl, et al., "Effects of flunarizine on Metrazol-induced seizures in developing rats," Epilepsy Res., 1(5):302-5 (1987).
Porter et al., "Report of a parent survey of cannabidiol-enriched cannabis use in pediatric treatment-resistant epilepsy," Epilepsy Behav., 29(3):574-577 (2013).
Porter et al., "Randomized, multicenter, dose-ranging trial of retigabine for partial-onset seizures," Neurology, 68(15):1197-1204 (2007).
Potter, "Cannabis Horticulture," Chapter 4, Handbook of Cannabis, ed. Roger G. Pertwee, pp. 65-88 (2014).
Potter, C., "Cannabis Extract Brings Hope for Children with Epilepsy," Dec. 3, 2013, 3 pages.
Poortman-Van Der Meer, "A contribution to the improvement of accuracy in the quantitation of THC," Forensic Science International, Apr. 1999, 101(1):1-8.
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://

(56) References Cited

OTHER PUBLICATIONS www.ctvnews.ca/health/health-headlines/pot-or-not-why-parents-of-kids-with-epilepsy-want-access-to-marijuana-treatment-1.1372695?cache=.
Pouton, "Lipid formulations for oral administration of drugs: non-emulsifying, self-emulsifying and 'self-micro emulsifying' drug delivery systems," Eur J Pharm Sci, 11(Suppl. 2): S93-S98 (2000).
Press, et al., "Parental reporting of response to oral cannabis extracts for treatment of refractory epilepsy," Epilepsy Behav. Apr. 2015; 45:49-52. doi: 10.1016/j.yebeh.2015.02.043. Epub Apr. 3, 2015.
Pruitt et al., "Ethanol in Liquid Preparations Intended for Children," Pediatrics, 73(3):405-407 (1984).
Purcarin, G. & Ng, Y -T., "Experience in the use of clobazam in the treatment of Lennox-Gastaut syndrome," Ther Adv Neurol Disord 2014, vol. 7(3):169-176.
Raab et al., "Multiple myeloma," Lancet, 374(9686):324-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ragona, F. et al., "Dravet syndrome: early clinical manifestations and cognitive outcome in 37 Italian patients," Brain Dev., 32:71-77 (2010).
Ramantani, et al. "Epilepsy in Aicardi—Goutieres syndrome," Official J Eur Paediatric Neurology Society, 18:30-37 (2014).
Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HT1A receptors are involved in the cannabidiol-induced attenuation of behavioural and cardiovascular responses to acute restraint stress in rats," Br J Pharmacol. Jan. 2009;156(1): 181-8.
Reply to EPO Communication in European Patent No. EP2448637, dated Nov. 2, 2016, 45 pages.
Reply to Opponent's Written Submission in European Patent No. EP2448637, dated Nov. 4, 2016, 13 pages.
Reply to Opponent's Written Submission in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Romano et al., "Inhibition of colon carcinogenesis by a standardized Cannabis sativa extract with high content of cannabidiol," Phytomedicine, 21:631-639 (2014).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Russo, "Taming THC: potential cannabis synergy and phytocannabinoid-termoid entourage effects," British J. of Pharm. 1333 (2011), 21 pages.
Russo et al., "Upholding WAG/Rij Rats as a Model of Absence Epileptogenesis: Hidden Mechanisms and a New Theory on Seizure Development, Neuroscience and Biobehavioral Reviews," 71:388-408 (2016).
Rubio, et al. "In vivo Experimental Models of Epilepsy," Central Nervous System Agents in Medicinal Chemistry, 10:298-309, 2010.
Sadanandasarma et al., Rasatarangini. 11th Ed. 1979:720-3. Sanskrit, 8 pages.
Sander, "The epidemiology of epilepsy revisited." Curr Opin Neural. Apr. 2003; 16(2): 165-70.
Sastri et al., Anandakandam. 1st Edition. 1952:241. Sanskrit, 5 pages.
Schafroth, M. A. et al., "Stereodivergent Total Synthesis of Δ9-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.
Scuderi et al., "Cannabidiol in medicine: a review of its therapeutic potential in CNS disorders," Phytother Res., 23(5):597-602 (2009).
Shih, J. J. et al., "Epilepsy treatment in adults and adolescents: Expert opinion, 2016," Epilepsy & Behavior, 69:186-222 (2017).
Shukla. [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Position Statement on the Use of Medical Cannabis for the Treatment of Epilepsy in Canada," Can J. Neurol. Sci., 33:783-786 (2006).
Silva, R. et al., "Clobazam as Add-on Therapy in Children with Epileptic Encephalopathy," Can. J. Neurol. Sci., 33:209-213 (2006).
Smith, R. M., "Identification of Butyl Cannabinoids in Marijuana," Journal of Forensic Sciences, 42:610-618 (1997).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Statement of Opposition for EP10734541.5, mailed Dec. 5, 2014, 20 pages.
Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017, 20 pages.
Statement of Grounds of Appeal for European Application No. 10734541.5 on behalf of the Proprietors: GW Pharma Limited and Otsuka Pharmaceutical CO Limited, dated Apr. 12, 2017, 6 pages.
Sun et al., "Comparative study of organic solvent and water-soluble lipophilic extractives from wheat straw I: yield and chemical composition," J Wood Sci, 49:47-52 (2003).
Smith, R. M. & Kempfert, K. D., "Δ1-3,4-CIS-Tetrahydrocannabinol in Cannabis Sativa," Phytochemistry, 16:1088-1089 (1977).
Specchio, L. M. & Beghi, E., "Should Antiepileptic Drugs Be Withdrawn in Seizure-Free Patients?" CNS Drugs, 18(4):201-212 (2004).
Stewart, K., "Families migrating to Colorado for a medical marijuana miracle," Nov. 11, 2013, 8 pages; https://archive.sltrib.com/article.php?id=57052556&itype=CMSID.
Stewart, K., "University of Utah doctors: Say 'yes' to cannabis oil for kids," by Kirsten Stewart the Salt Lake Tribune, Nov. 13, 2013, 4 pages.
Stinchcomb, A. L. et al., "Human skin permeation of $\Delta^9$-tetrahydrocannabinol, cannabidiol and cannabinol," JPP 2004, 56: 291-297.
Thiel, E. A., "Managing Epilepsy in Tuberous Sclerosis Complex," J Child Neurol 2004;19:680-686.
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi,seizures%20stopped%20for%20seven%20days.&text=The%20marijuana%20strain%20Charlotte%20and,has%20been%20named%20after%20her.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Supplemental Expert Statement of Professor Benjamin J. Whalley, dated Nov. 4, 2016, 9 pages.
Swann et al., The effects of seizures on the connectivity and circuitry of the developing brain. Ment Retard Dev Disabil Res Rev. 2004; 10(2):96-100.
Third Party Observations for Application No. AU20 I 2314128, mailed Mar. 19, 2015, 51 pages.
Third Party Observations for Application No. EP10734541.5, mailed Apr. 3, 2017, 19 pages.

(56) References Cited

OTHER PUBLICATIONS

Third Party Observations for Application No. EP1712658.1, mailed Nov. 22, 2013, 14 pages.
Third Preliminary Amendment under 37 C.F.R. 1.115 for U.S. Appl. No. 13/380,305, dated May 23, 2014, 4 pages.
Thomas et al., "Evidence that the plant cannabinoid Delta9-tetrahydrocannabivarin is a cannabinoid CB1 and CB2 receptor antagonist," Br J Pharmacol., 146(7):917-926 (2005).
Thompson et al., "Comparison of acute oral toxicity of cannabinoids in rats, dogs and monkeys," Toxicology and Applied Pharmacology, vol. 25, Issue 3, pp. 363-372 (1973).
Thurman et al., "Standards for epidemiologic studies and surveillance of epilepsy," Epilepsia, 52 (Suppl 7):2-26 (2011).
Thumma et al., "Influence of plasticizers on the stability and release of a prodrug of ./19-tetrahydrocannabinol incorporated in poly(ethylene oxide) matrices," Eur J Pharmaceutics and Biopharmaceutics, 70(2):605-614 (2008).
Thurstone, "Avoid Charlotte's Web for Epilepsy," Jun. 26, 2014, URL <http://drthurstone.com/charlotted-web-not-safest-option-epilepsy-treatment/>, 4 pages.
Tose, L. V. et al., "Isomeric separation of cannabinoids by UPLC combined with ionic mobility mass spectrometry (TWIM-MS)—Part I," International Journal of Spectrometry, 418:112-121 (2016).
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Trost, B. M. & Dogra, K., "Synthesis of (-)-Δ9-trans-Tetrahydrocannabinol: Stereocontrol via Mo-Catalyzed Asymmetric Allylic Alkylation Reaction," Organic Letters, 9(5):861-863 (2007).
Turkanis et al., "An Electrophysiological Analysis of the Anticonvulsant Action of Cannabidiol on Limbic Seizures in Conscious Rats," Epilepsia., 20:351-363 (1979).
Uliss et al., "The conversion of 3,4-CIS- to 3,4-TRANS-cannabinoids," Tetrahedron, 34:1885-1888 (1978).
Usami et al., "Synthesis and pharmacological evaluation in mice of halogenated cannabidiol derivatives," Chem Pharm Bull (Tokyo), 47(11):1641-1645 (1999).
"Marinol®," label retrieved from: <https://www.accessdata.fda.gov/dmgsatfda docs/label/2006/018651 s025s026lbl.pdf>, 11 pages.
Utah.gov [online], "2nd Agenda Controlled Substances Advisory Committee Meeting," Nov. 12, 2013, URL <https://www.utah.gov/pmn/files/81459.pdt>, 63 pages.
Van Bakel et al., "The draft genome and transcriptome of *Cannabis sativa*," Genome Biology 2011, 12:R102, 18 pages; http://genomebiology.com/2011/12/10/R102 (Oct. 24, 2011).
Van Rijckevorsel, "Treatment of Lennox-Gastaut syndrome: overview and recent findings," Neuropsychiatr Dis Treat. Dec. 2008; 4(6): 1001-1019.
Van Straten et al., "Update on the Management of Lennox-Gastaut Syndrome," Pediatric Neurology, 47:153-161 (2012).
Velasco et al., "Anticancer mechanisms of cannabinoids," Curr Oncol, 23(2):S23-S32 (2016).
Velisek, "Models of Chemically-Induced Acute Seizures," Models Seizure Epilepsy, 127-152 (2006).
Veliskova, Chapter 48 "Behavioral Characterization of Seizures in Rates," Model Seizures Epilepsy, 601-611 (2006).
Vollner et al., Haschisch XX: Cannabidivarin, ein neuer Haschisch-Inhaltsstoff. Tetrahedron Lett. 1969;10(3):145-7.
Wahle et al., "Development of tolerance to the anticonvulsant effect of valproate but not to ethosuximide in a rat model of absence epilepsy," Eur J Pharma. May 1990;181(1-2):1-8.
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol. Sep. 28, 2001;428(1):51-7.

Weed Wars, Video I, Dec. 10, 2011, Weed Wars: The Story of Jayden-Andrew DeAngelo; https://www.youtube.com/watch?v=2WizdR5uHj0.
Weed Wars, Video II, May 25, 2013, 3 pages; available at https://www.youtube.com/watch?v=XBX_DB9sw5U.
WeedWars, CNN Special, Decriminialise It, Dr. Sanjay Gupta, 2013; https://www.youtube.com/watch?v=Z3IMfl1_K6U, 8 pages.
Nathaniel Morris (of Weed Country on Discovery Channel), Selected Media Examples of Pediatric Applications of Cannabidiol, 2013, 6 pages; available at https://www.youtube.com/watch?v=Mw3wiWkbRg8.
Weimer-Kruel, A. et al., "Cannabidiol Interacts Significantly with Everolimus-Report of a Patient with Tuberous Sclerosis Complex," Neuropediatrics, 50(6), 2019, 4 pages; doi:https://doi.org/10.1055/s-0039-1695786.
Weston et al., "Tetrahydrocannabivarin exhibits anticonvulsant effects in a piriform cortical brain slice model of epileptiform activity." Pro British Pharm Soc 75th Anniv Meeting. Dec. 31, 2006 Found on: http://www.pA2online.org/abstract/abstract.jsp?abid=28533. Abstract Only. 1 Page.
Whittle et al., (2001). Prospects for New Cannabis-Based Prescription Medicines. Journal of Cannabis Therapeutics. 1(3-4); doi:10.1300/J175v01, 1(3-4), 23 pages.
Wilkey, R., "'Weed Wars': Five-Year-Old Takes Medical Marijuana on Reality Show (Video)", Dec. 10, 2011, 7 pages; https://www.huffpost.com/entry/weed-wars-five-year-old-smokes-marijuana_n_1140351.
Wingerchuk, "Cannabis for medical purposes: cultivating science, weeding out the fiction," Lancet. Jul. 24-30, 2004;364(9431):315-6.
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhornitsky & Potvin, "Cannabidiol in Humans—The Quest for Therapeutic Targets," Pharmaceuticals, 5:529-552 (2012).
Zhao et al., "Chapter 27: Repetitive Seizures in the Immature Brain," Models of Seizures and E[epilepsy, 341-350 (2006).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
Notice of Opposition to European Patent Application No. EP18737374.1, Patent No. EP3641819, dated Jul. 12, 2024, 23 pages.
Afternoon Session, Panel 1—Living with TSC and LAM, Offical Transcript (Part 3 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 24 pages.
Afternoon Session, Panel 2—Current and Future Approaches to Treating TSC and LAM, Offical Transcript (Part 4 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 17 pages.
[No Author Listed] The Voice of the Patient, A Report from the Tuberous Slerosis Alliance's Externally-Led Patient-Focused Drug Development Meeting, Report Date: Oct. 26, 2017, Public Meeting Jun. 21, 2017, 79 pages.
Conference Book of the 2017 International Research Conference on TSC and LAM: Innovating Through Partnerships, Washington, D.C., Jun. 22-24, 2017, 160 pages.
Devarbhavi, "An update on drug-induced liver injury," J. Clinical and Experimental Hepatology, 2(3):247-259 (2012.

(56) References Cited

OTHER PUBLICATIONS

Franz, D. N. & Capal, J. K., "mTOR inhibitors in the pharmacologic management of tuberous sclerosis complex and their potential role in other rare neurodevelopmental disorders," Orphanet Journal of Rare Diseases, 12:51 (2017), 9 pages; doi: 10.1186/s13023-017-0596-2.
Kalenderoglou et al., "Cannabidiol Reduces Leukemic Cell Size—But Is It Important?" Front. Pharmacol., Mar. 24, 2017, Sec. Ethnopharmacology, vol. 8—2017, 9 pages; https://doi.org/10.3389/fphar.2017.00144.
Kelley, "Medical Cannabis Community Wants to Remain Apart," Kitsap Peninsula Business Journal, Apr. 3, 2013; available at https://www.420magazine.com/community/threads/medical-cannabis-community-wants-to-remain-apart.186955/, 4 pages.
Klonopin® Tablets (clonazepam) Klonopin® Wafers (clonazepam orally disintegrating tablets) Product Label, revised Apr. 4, 2009, 18 pages.
Krueger et al., "Tuberous Sclerosis Complex Surveillance and Management: Recommendations of the 2012 International Sclerosis Complex Consensus Conference," Pediatric Neurology, 49:255-265 (2013).
Morning Session, Panel 1—Living with TSC and LAM, Offical Transcript (Part 1 of 4) of the Video "Externally-Led Patient-Focused Drug Development Meeting," Silver Springs, Maryland, Jun. 21, 2017, available on You Tube at https://www.youtube.com/watch?v=qoxOKR3WpFs, 26 pages.
Morning Session, Panel 2—Current and Future Treatments for TSC, Offical Transcript (Part 2 of 4) of the Video "Externally-Led Patient-Focused Drug Development Meeting," Silver Springs, Maryland, Jun. 21, 2017, available on You Tube at https://www.youtube.com/watch?v=goxOKR3WpFs, 19 pages.
Peron, A. et al., Agenda Program and Description of the "2nd Early Tuberous Slerosis Complex Researcher Meeting," Washington, DC, Jun. 21, 2017, 6 pages.
Rosenkrantz et al., "Toxicity of Short-Term Administration of Cannabinoids to Rhesus Monkeys," Toxicology and Applied Pharmacology, 58:118-131 (1981).
Shrivastava et al., "Cannabidiol Induces Programmed Cell Death in Breast Cancer Cells by Coordinating the Cross-talk Between Apoptosis and Autophagy," Mol Cancer Ther; 10(7):1161-1172 (2011).
Aagaard, L. et al., "Adverse Drug Reactions in the Paediatric Population in Denmark: A Retrospective Analysis of Reports Made to the Danish Medicines Agency from 1998 to 2007," Drug Saf, 33(4):327-339 (2010).
Anderson, C. L., "An Evaluation of Effectivness of Cannabidiol as an Antiepileptic Drug for Children with Intractable Generalized Epilepsy," Dissertation, University of Florida, 2017, 130 pages; https://ufdc.ufl.edu/UFE0050852/00001/pdf.
Ben-Ari, Y., "Seizures Beget Seizures: The Quest for GABA as a Key Player," Critical Reviews in Neurobiology, 18(1-2):135-144 (2006).
Chesney et al., "Adverse effects of cannabidiol: a systematic review and meta-analysis of randomized clinical trials," Neuropsychopharmacol., 45:1799-1806 (2020); https://doi.org/10.1038/s41386-020-0667-2.
Consroe, P. & Wolkin, A., "Cannabidiol—antiepileptic drug comparisons and interactions in experimentally induced seizures in rats," J Pharmacol Exp Ther. Apr. 1977;201(1):26-32.
Devinsky et al., "Cannabidiol efficacy independent of clobazam: Meta-analysis of four randomized controlled trials," Acta Neurol Scand., 142:531-540 (2020).
Epidiolex® (cannabidiol) oral solution, CV, Prescribing Information, 2021, 38 pages; https://www.accessdata.fda.gov/drugsatfda_docs/label/2021/210365Orig1s011lbl.pdf.
Epidiolex® (cannabidiol) oral solution, CV, Prescribing Information, 2024, 32 pages; https://pp.jazzpharma.com/pi/epidiolex.en.USPI.pdf.
Epidyolex 100 mg oral soluction, Summary of Product Characteristics, European Medicines Compendium, Sep. 2019, 19 pages; https://web.archive.org/web/20200920022105/https://www.medicines.org.uk/emc/product/10781/smpc.
Fabiano, V. et al., "Adverse drug reactions in newborns, infants and toddlers: pediatric pharmacovigilance between present and future," Expert Opinion on Drug Safety, 11(1): 95-105 (2011); doi: 10.1517/14740338.2011.584531.
Feierman, D. E. & Lasker, J. M., "Metabolism of fentanyl, a synthetic opioid analgesic, by human liver microsomes. Role of CYP3A4," Drug Metabolism and Disposition, 24(9):932-939, Sep. 1996, Abstract. https://dmd.aspetjournals.org/content/24/9/932, 4 pages.
Gaston, T. E. et al., "Cannabis for the Treatment of Epilepsy: An Update," Curr Neurol Neurosci Rep., 18(11):73 (2018), 9 pages; doi: 10.1007/s11910-018-0882-y.
Gauthier et al., "Clobazam: A Safe, Efficacious, and Newly Rediscovered Therapeutic for Epilepsy," CNS Neurosci Ther., 21(7):543-548 (2015); doi: 10.1111/cns.12399. Epub Apr. 28, 2015.
Gunning et al., "Cannabidiol in conjunction with clobazam: analysis of four randomized controlled trials," Acta Neurol Scand., 143:154-163 (2021).
Manini et al., "Safety and Pharmacokinetics of Oral Cannabidiol When Administered Concomitantly With Intravenous Fentanyl in Humans," J Addict Med., 9(3): 204-210 (2015); doi:10.1097/ADM.0000000000000118.
Morrison et al., "A Phase 1 Investigation Into the Potential Effects of Cannabidiol on CYP3A4-Mediated Drug-Drug Interactions in Healthy Volunteers," Abstract No. 1.297, Submission ID: 500033, Presentation Date: Dec. 1, 2018, Published Date: Nov. 5, 2018; https://aesnet.org/abstractslisting/a-phase-1-investigation-into-the-potential-effects-of-cannabidiol-on-cyp3a4-mediated-drug-drug-interactions-in-healthy-volunteers, 2 pages.
Morrison et al., "A Phase 1, Open-Label, Pharmacokinetic Trial to Investigate Possible Drug-Drug Interactions Between Clobazam, Stiripentol, or Valproate and Cannabidiol in Healthy Subjects," Clinical Pharmacology in Drug Development, 8(8):1009-1031 (2019).
Patsalos et al., "Clinical implications of trials investigating drug-drug interactions between cannabidiol and enzyme inducers or inhibitors or common antiseizure drugs," Epilepsia, 61:1854-1868 (2020).
Devinsky et al., Trial Protocol, Supplementary Material to "Trial of Cannabidiol for Drug-Resistant Seizures in the Dravet Syndrome," N Engl J Med, 376(21):2011-2020 (2017), 426 pages.
Devinsky, O. et al., "Trial of Cannabidiol for Drug-Resistant Seizures in the Dravet Syndrome," N Engl J Med, 376(21):2011-2020 (2017).
[No Author Listed], European Medicines Agency (EMA), "Public summary of opinion on orphan designation—Cannabidiol for the treatment of Dravet syndrome," Nov. 10, 2014, https://www.ema.europa.eu/en/documents/orphandesignation/eu3141339-public-summary-opinion-orphan-designation-cannabidiol-treatment-dravetsyndrome-en.pdf, 4 pages.
Notice of Opposition to European Patent Application No. EP19702670.1, Patent No. EP3743053, dated Aug. 27, 2024, 22 pages.
Perucca, "Cannabinoids in the Treatment of Epilepsy: Hard Evidence at Last?" Journal of Epilepsy Research, 7(2):61-76 (2017).
Vezyroglou, K. & Cross, J. H., "Targeted Treatment in Childhood Epilepsy Syndromes," Curr Treat Options Neurol, 18:29 (2016), Published online May 7, 2016. doi: 10.1007/s11940-016-0407-4,12 pages.
Wirrell, E. C., "Treatment of Dravet Syndrome," Can J Neurol Sci., 43:S13-S18 (2016).
Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p0240 Abstract, 1 page.

\* cited by examiner

Figure 1. The effect of CBD on wound healing in Tsc2-/-Mouse Embryonic Fibroblast and AML cell lines.
A
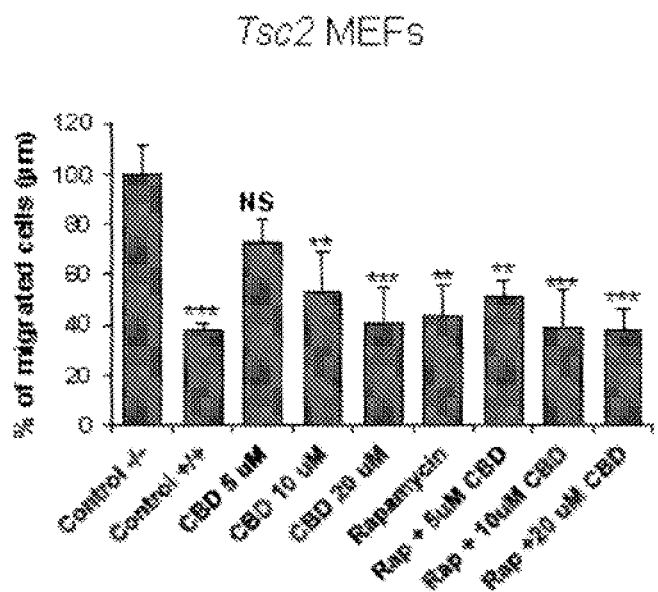
B
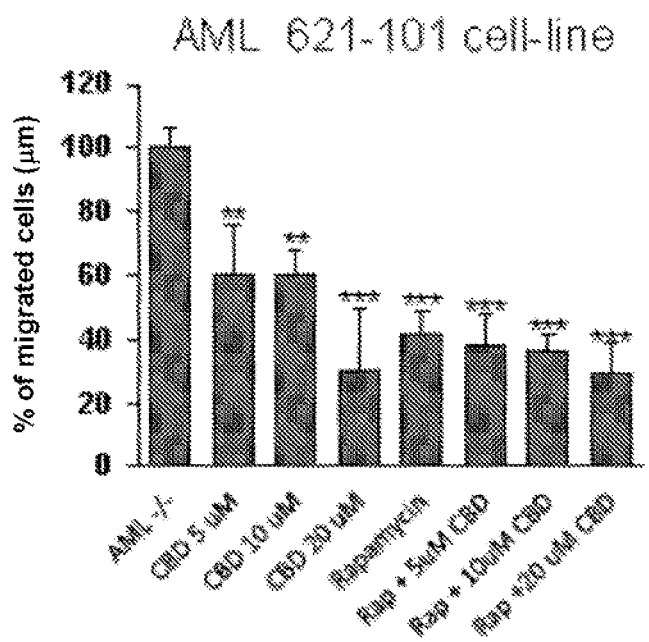

Figure 2. The effect of CBD on migration and invasion in Tsc2-/-Mouse Embryonic Fibroblast and AML cell lines.
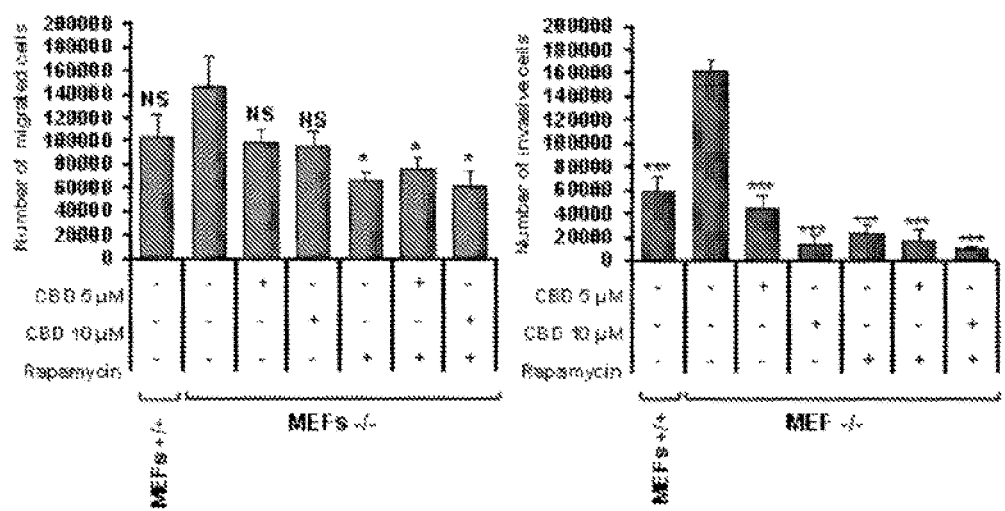
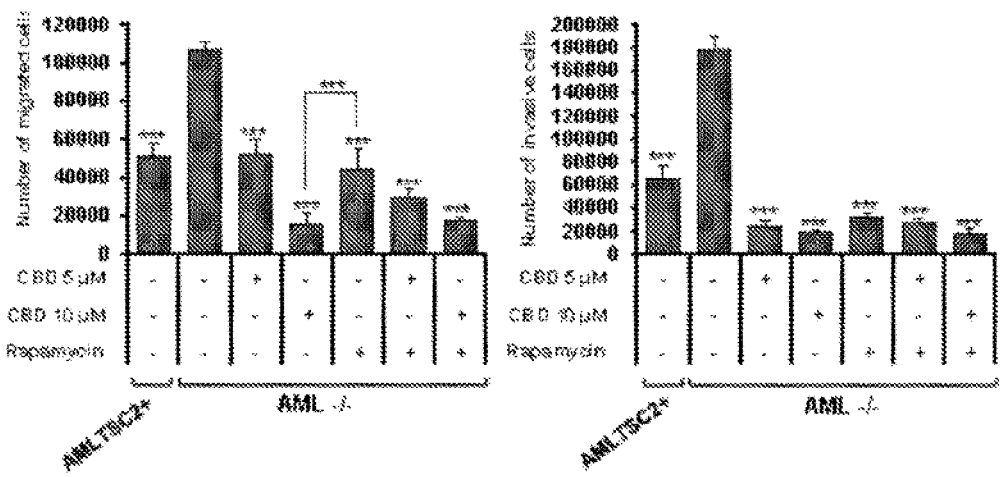

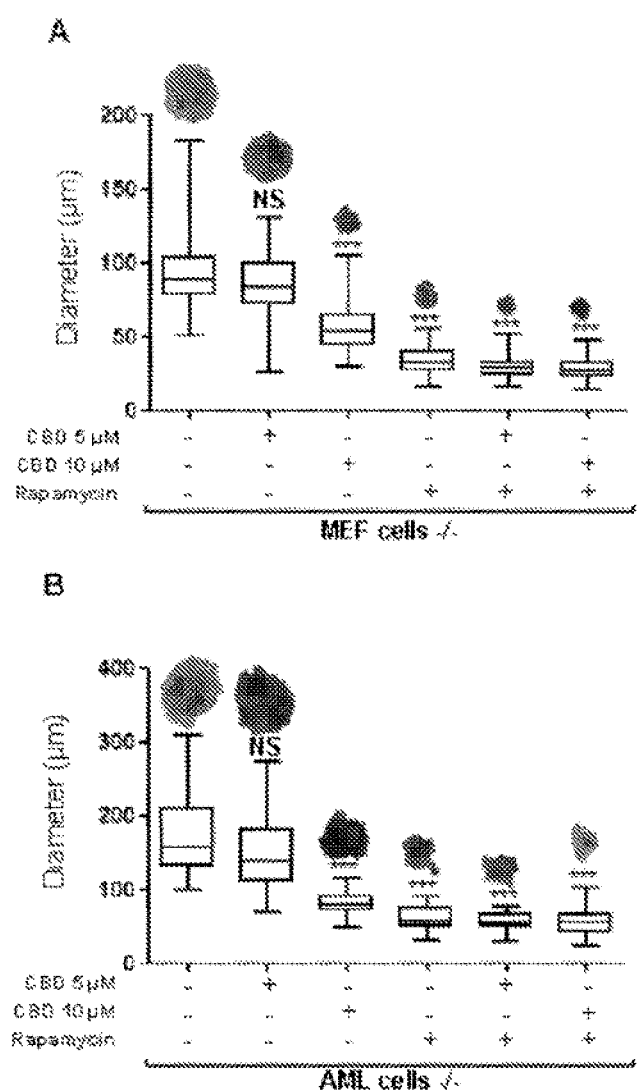
Figure 3. The effect of CBD on tumour formation in Tsc2-/-Mouse Embryonic Fibroblast (A) and AML (B) cell lines.

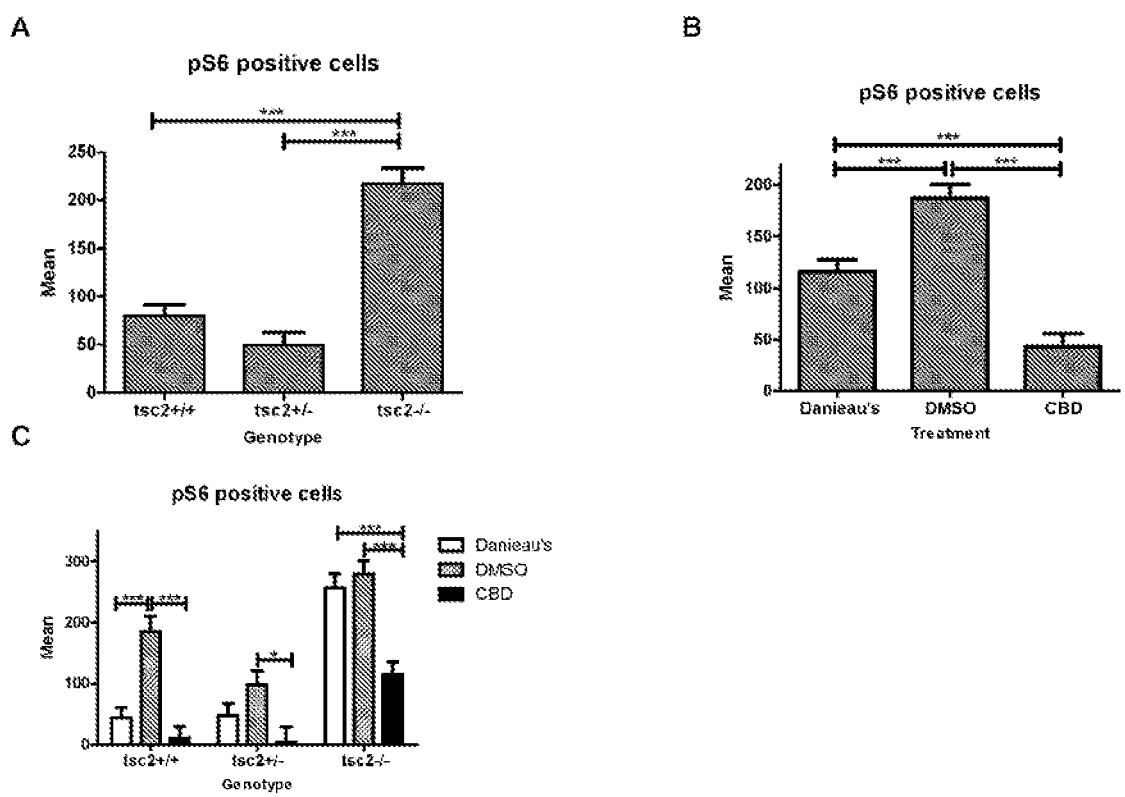
Figure 4. The effect of CBD on the number of pS6 positive cells in a zebrafish model of TSC

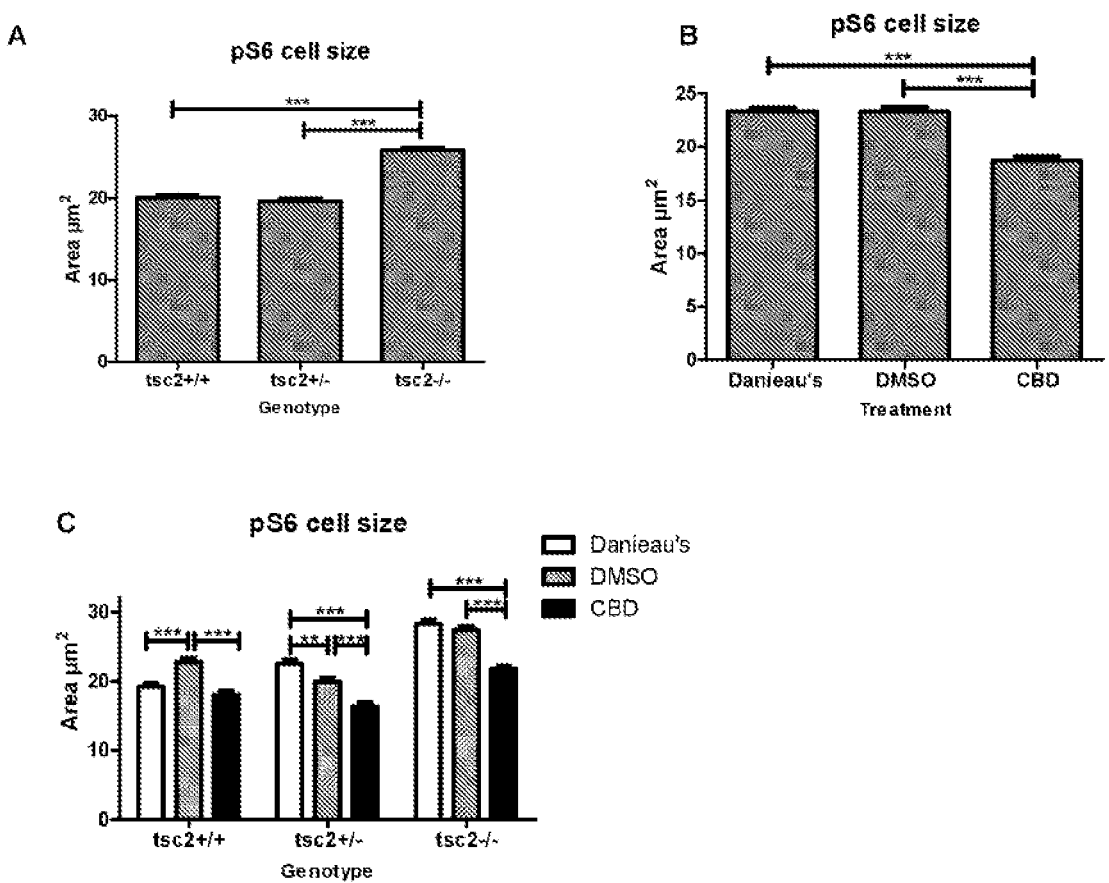
Figure 5. The effect of CBD on the size of pS6 cells in a zebrafish model of TSC Figure 6. The effect of CBD on inhibition of growth in PANC1 (A) and MIAPACA(B) cell lines
A
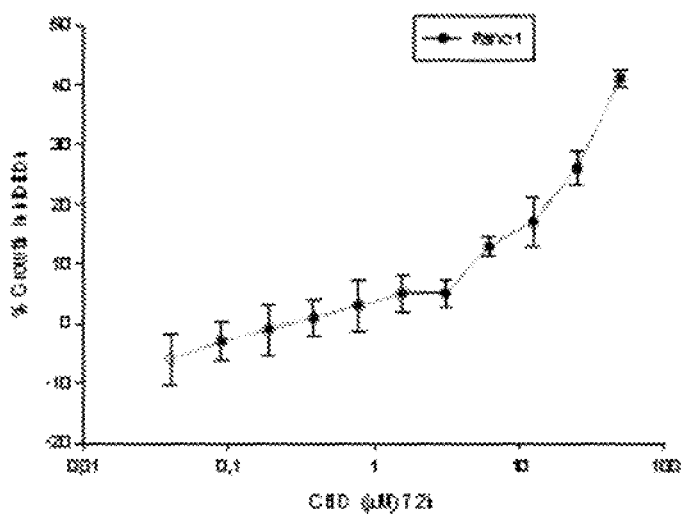
B
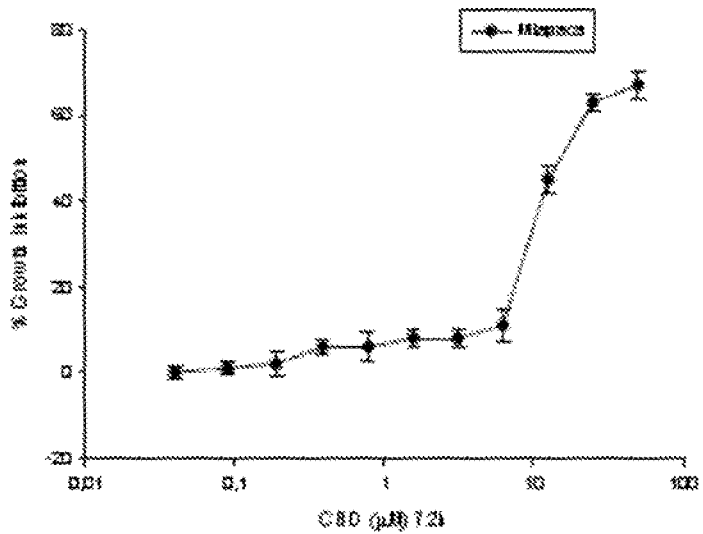

USE OF CANNABIDIOL IN THE TREATMENT OF TUBEROUS SCLEROSIS COMPLEX

The present invention relates to the use of cannabidiol (CBD) for the treatment of tumours associated with Tuberous Sclerosis Complex (TSC). In particular the CBD was able to decrease the number and size of marker cells, pS6, in a zebrafish model of TSC. This is suggestive of a disease modifying effect whereby treatment with CBD could result in the reduction or prevention of the benign tumours that occur in TSC patients.

Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD is given concomitantly with one or more other drugs used in the treatment of TSC. Such drugs may include rapamycin and/or everolimus. Alternatively the CBD may be formulated for administration separately, sequentially or simultaneously with one or more drugs used in the treatment of TSC or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Tuberous sclerosis complex (TSC) is an autosomal dominant neurocutaneous disorder characterized by the formation of hamartomas in multiple organ systems, most notably the brain, skin, kidneys, heart and eyes (Leung 2007). A hamartoma is a benign tumour composed of an overgrowth of mature cells and tissues normally found at the site that are grown in a disorganized mass. The benign tumours, also referred to as tubers, are descriptive of the potato-like nodules in the brain, which calcify with age and become sclerotic (Leung 2007).

The disease caused by a mutation in either the TSC1, coding the protein hamartin, or the TSC2, coding tuberin, genes (Curatolo 2015). Hamartin and tuberin form a complex that, due to its GTPase-activating protein (GAP) domain, keeps Rheb bound to GDP. When a mutation in either of these proteins is present, the inhibitory function of this complex is impaired, allowing constitutive phosphorylation of mTOR (Laplante & Sabatini 2012; Dibble et al. 2012).

Symptoms of the disorder vary depending on which system and which organs are involved. The natural course of TSC varies from individual to individual, with symptoms ranging from very mild to quite severe. Tumours can grow in nearly any organ, but they most commonly occur in the brain, kidneys, heart, lungs, and skin.

When present, neurologic complications are the most common cause of mortality and morbidity and are the most likely to affect quality of life. Seizures and epilepsy are the most common forms of neurologic complication and occur in 75-90% of patients (Leung 2007). Sixty-three percent of patients experience seizure onset within the first year of life (Wang & Fallah 2014).

The most common types of seizures in TSC patients are infantile spasms, complex partial seizures, and generalized tonic clonic seizures (Leung 2007). Refractory epilepsy develops in 55-62.5% of patients (Wang & Fallah 2014).

Three types of brain lesions are seen in TSC: cortical tubers, for which the disease is named, generally form on the surface of the brain but may also appear in the deep areas of the brain; subependymal nodules (SEN), which form in the walls of the ventricles, the fluid-filled cavities of the brain; and subependymal giant-call astrocytomas (SEGA), which develop from SEN and grow such that they may block the flow of fluid within the brain, causing a build-up of fluid and pressure and leading to headaches and blurred vision.

Tumours called cardiac rhabdomyomas are often found in the hearts of infants and young children with TSC. If the tumours are large or there are multiple tumours, they can block circulation and cause death.

Benign tumours called phakomas are sometimes found in the eyes of individuals with TSC, appearing as white patches on the retina. Generally they do not cause vision loss or other vision problems, but they can be used to help diagnose the disease. Additional tumours and cysts may be found in other areas of the body, including the liver, lung, and pancreas. Bone cysts, rectal polyps, gum fibromas, and dental pits may also occur.

Patients with TSC are commonly treated with anti-seizure medications to control epilepsy; in addition tumours are treated with mTOR inhibitors.

Only one drug, an mTOR inhibitor (everolimus) has been FDA approved for the treatment of TSC in the 165 years the disease has been identified, and it is specifically indicated for the treatment of sub-ependymal giant cell astrocytoma associated with TSC, where treatment is required, and where surgery is not considered appropriate. The therapeutic dose of everolimus is 4.5 mg/m$^2$.

Everolimus has a high risk side effect profile and may not be suitable for use in all patients with TSC. As cited in the Prescribing Information, "clinical benefit such as improvement in disease-related symptoms has not been demonstrated" (Novartis 2015).

The side effect profile of everolimus includes non-infectious pneumonitis; immunosuppression; increased risk of infections; angioedema; oral ulceration; renal failure; impaired wound healing; elevations of serum creatinine, urinary protein, blood glucose, and lipids; decreases in haemoglobin, neutrophils, and platelets.

The most common adverse reactions (incidence ≥30%) include stomatitis, infections, rash, fatigue, diarrhoea, oedema, abdominal pain, nausea, fever, asthenia, cough, headache and decreased appetite (Novartis 2015).

Tuber growth is a hallmark of TSC presentation. In addition to mTOR inhibition, which may contribute to reduction in tuber size in patients with TSC, overexpression of hypoxia-inducible factor-1 (HIF1α) and vascular endothelial growth factor (VEGF) are thought to be the cause of these tubers. These growth factors are involved in the angiogenesis pathway and correlate with the mutation of TSC1 and TSC2 as well as the extent of tuber growth in animal models of TSC. It is unknown if these actions are downstream of the modulation of mTOR by CBD, or by a distinct signalling pathway. Rapamycin or related inhibitors of mTOR may have therapeutic benefit in TSC both by direct tumour cell killing and by inhibiting the development of TSC lesions through impairment of VEGF production.

The compound cannabidiol (CBD) has recently been used in several treatment resistant paediatric epilepsy clinical trials, where significant reductions in seizure frequency were reported (Devinsky et al. 2014). Furthermore CBD has been shown to be beneficial in the treatment of refractory epilepsy in TSC patients having focal onset seizures (Geffrey et al., 2014).

Whilst the potential of cannabis and the cannabinoids, including CBD, to treat epilepsy has been rekindled, to date the ability of the compound to treat the tumours associated with TSC or indeed to provide a disease modifying effect has not been shown.

The applicant has found that CBD was able to reduce TSC tumour cells in both an in vitro TSC cell line and in vivo in a zebrafish model. Furthermore CBD has been shown to act in a synergistic manner with an mTOR inhibitor, rapamycin, in a tumour cell line.

Therefore CBD has been shown to treat the benign tumours associated with TSC. Such an ability to reduce or prevent the formation of these benign tumours results in a disease modifying effect. This effect comes about due to the reduction of the size or the prevention of formation of the benign tumours thereby prevents the co-morbid symptoms associated with TSC such as seizures which are caused by the benign tumours growing in the brain.

BRIEF SUMMARY OF THE DISCLOSURE

In accordance with a first aspect of the present invention there is provided cannabidiol (CBD) for use in the treatment of tumours associated with Tuberous Sclerosis Complex (TSC).

Preferably the tumours associated with TSC are benign tumours. More preferably, the size of the tumours associated with TSC are reduced. Alternatively, the CBD is provided at a dose suitable to inhibit the formation of the tumours associated with TSC.

Preferably the CBD is used in combination with one or more concomitant drugs used in the treatment of TSC. More preferably the one or more concomitant drugs used in the treatment of TSC is an mTOR inhibitor. More preferably still the mTOR inhibitor is rapamycin or everolimus.

Preferably the CBD is present as a highly purified extract of cannabis which comprises at least 95% (w/w) CBD. Preferably the extract comprises less than 0.15% THC. More preferably the extract further comprises up to 1% CBDV.

Alternatively the CBD is present as a synthetic compound.

Preferably the dose of the one or more concomitant drugs used in the treatment of TSC that are used in combination with the CBD is reduced.

Preferably the dose of CBD is greater than 5 mg/kg/day.

In accordance with a second aspect of the present invention there is provided a method of treating a patient with Tuberous Sclerosis Complex (TSC) comprising administering cannabidiol (CBD) in a therapeutically effective amount to prevent or reduce tumours associated with TSC to the patient in need thereof.

BRIEF DESCRIPTION OF THE DRAWINGS

Embodiments of the invention are further described hereinafter with reference to the accompanying drawings, in which:

FIG. 1 shows the effect of CBD on wound healing in Tsc2-/-Mouse Embryonic Fibroblast (A) and AML cell lines (B);

FIG. 2 shows the effect of CBD on migration and invasion in Tsc2-/-Mouse Embryonic Fibroblast (A) and AML (B) cell lines;

FIG. 3 shows the effect of CBD on tumour formation in Tsc2-/-Mouse Embryonic Fibroblast (A) and AML (B) cell lines;

FIG. 4 shows the effect of CBD on the number of pS6 positive cells in a zebrafish model of TSC;

FIG. 5 shows the effect of CBD on the size of pS6 cells in a zebrafish model of TSC; and FIG. 6 shows the effect of CBD on inhibition of growth in PANC1 (A) and MIAPACA(B) cell lines.

DEFINITIONS

Definitions of some of the terms used to describe the invention are detailed in Table 1 below:

The cannabinoids described in the present application are listed below along with their standard abbreviations.

TABLE 1

| Cannabinoids and their abbreviations | | |
|---|---|---|
| CBD | Cannabidiol | 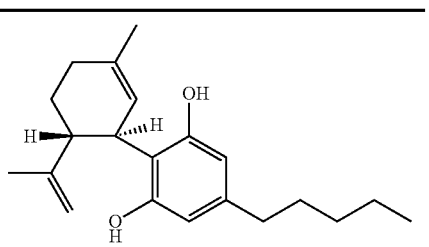 |
| CBDA | Cannabidiolic acid | 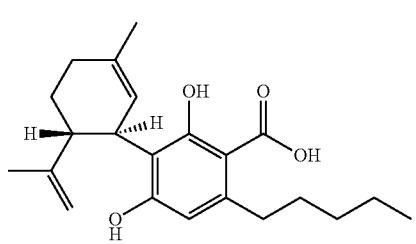 [SMILES: C=C(C)[C@@H]1CCC(C)=C[C@H]1c1c(O)cc(CCCCC)c(C(=O)O)c1O] |

TABLE 1-continued

Cannabinoids and their abbreviations

CBDV    Cannabidivarin

CBDVA    Cannabidivarinic acid

THC    Tetrahydrocannabinol

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

DETAILED DESCRIPTION

The following examples provide evidence for the efficacy of CBD in the ability to treat tumours in TSC. Example 1 tests CBD in two different TSC cell lines: (i) Angiomyolipomas 621-101 cell-line (derived from a Tuberous Sclerosis Complex patient with a known loss of function of TSC2), and (ii) Tsc2−/− and Tsc2+/+ mouse embryonic fibroblast (MEF) cell lines.

Example 2 describes a TSC model in zebrafish (Kim et al. 2011). CNS development in zebrafish follows the same pattern as in other vertebrates, with both neurons and glial cells having been identified.

Lastly, Example 3 demonstrates the synergistic action of CBD with an mTOR inhibitor, everolimus, in tumour cell lines.

Example 1: Efficacy of Cannabidiol in Reduction of Tumours in Two Tuberous Sclerosis Complex Cell Lines Materials and Methods Cell Lines and Maintenance (i) Angiomyolipomas (AML) cells derived from a Tuberous Sclerosis Complex patient (621-101 cell-line), with a known loss of function of TSC2. To generate a rescue control cell line, these 621-101 cells were stably transfected with a TSC2-expressing plasmid possessing Zeocin™ resistance (pcDNA3.1zeo-hTSC2). Zeocin™ was purchased from LifeTechnologies (cat no: R25001) and was used to originally generate the stable cell line (by Prof. Lisa Henske) over two weeks of Zeocin™ selection and then for continued maintenance of the cells in tissue culture (at 100 μg/ml).

(ii) Tsc2−/− p53−/− and Tsc2+/+p53−/− mouse embryonic fibroblast (MEF) cell lines (now referred to as Tsc2−/− and Tsc2+/+, respectively).

Cell Culture

Tsc2−/− and Tsc2+/+ cell lines were cultured and maintained in DMEM supplemented with 10% (v/v) FBS and 1% (v/v) penicillin-streptomycin in a humidified incubator (5% $CO_2$ at 37° C.). The AML −/− cell lines were cultured and maintained in DMEM supplemented with 15% (v/v) FBS and 1% (v/v) penicillin-streptomycin in a humidified incubator (5% $CO_2$ at 37° C.). For hypoxia, cells were put into a Binder CB150 hypoxic chamber set at 1% 02 for the indicated time points Drug Treatments Pure CBD was used in this example. Rapamycin was obtained from MerkMillipore.

The stock concentration of CBD was made to 20 mM in dimethyl sulfoxide (DMSO). CBD was added to culture media to final concentrations of either 5 µM or 10 µM, as indicated). The final concentration of the DMSO in the cell culture medium was at a maximum level of 0.05% (v/v).

Wound Healing Assays

Cells were seeded in 60 mm plates and left to reach 100% confluency. Cells were then synchronised in 1% (v/v) FBS DMEM for 24 h and "wounded" with a pipette tip. Dead cells were removed with PBS wash and then subsequently replaced with DMEM (10% (v/v) FBS). Cells were pre-treated for 30 min with either rapamycin, c-MET or STAT3 inhibitors (where indicated) before cytokine stimulation. Pictures were taken before treatment and 12-18 h after treatment using an inverted AMG EVOS microscope equipped with an Olympus camera.

Migration and Invasion Assays

Transwell permeable supports with 6.5 mm diameter inserts, 8.0 µm pore size, and a polycarbonate membrane were used to perform migration assays. Cells were grown in a 75-cm2 flask with standard medium (10% (v/v) FBS) until confluent. Cells were then harvested using Trypsin-EDTA. Cells were counted using a haemocytometer. A total of $1 \times 10^6$ cells and were resuspended in DMEM containing 1% (v/v) FBS. These cells were then seeded in the upper chamber of the Transwell; the lower chamber was filled with 600 mL of standard culture medium (10% (v/v) FBS) and 5 mg/mL fibronectin, as an adhesive substrate. Cells were incubated at 37° C. 5% $CO_2$ for 24 hours. The percentage of adherent cells was then determined by fixing the cells with methanol and acetone (1:1) for 20 minutes at 20° C. Cells were then stained with Crystal Violet (5 mg/mL) in ethanol for 10 minutes, followed by a stringent wash with dH2O until the water ran clear. Crystal Violet stained cells were eluted with 1% (w/v) SDS and the absorbance was read at 550 nm on a Genova MK3 Lifescience.

For invasion assays, a similar protocol was used; however, the top chamber of the Transwell was filled with 300 mL of BD Matrigel Basement Membrane Matrix (1 mg/mL). The Matrigel was incubated at 37° C. for 4 hours to allow it to gel. Cells were then seeded and incubated as described for migration assay for 3 days. The number of invaded cells was determined by fixation staining and elution of crystal violet with 1% (w/v) SDS, as before.

Tumour Spheroid Growth Assays

Two-layered soft agar assays were carried out in 6-well plates. All cell lines were plated in complete DMEM media in 0.35% (v/v) agar at $(3*10^5)$ over a 0.6% (v/v) agar layer. The agar was then overlaid with complete DMEM media and spheroids were grown for 14 days at 37° C. in 5% $CO_2$. Media were changed twice a week and new drug was added to media. Pictures were taken using an inverted AMG EVOS microscope equipped with an Olympus camera. Volume of tumour spheroids was measured using ImageJ software.

Lysing and Western Blot

Cells were washed in Phosphate Buffered Saline (PBS) and then lysed directly in sample buffer (62.5 mM Tris HCL, 50 mM DTT, 2% SDS (w/v), 10% Glycerol (w/v), 0.1% Bromophenol blue (w/v) pH 7.6) and sonicated for 5×20 s cycles on full power (30 amplitude microns). Samples were boiled at 95° C. for 10 min. Lysates were resolved by SDS-PAGE and proteins were transferred to polyvinylidene difluoride membranes.

Membranes were blocked in 5% (w/v) dry milk powder dissolved in Tris-buffered saline containing 0.1% (v/v) Tween, then probed with primary antibody and horse radish peroxidase-conjugated secondary antibody. Proteins were visualized using Enhanced Chemiluminescent solution and Hyperfilm. Antibodies towards ribosomal protein S6 (rpS6), phospho-rpS6 (Ser235/236) were purchased from Cell Signaling Technology. Anti-HIF-1α was obtained from BD transduction laboratories. Statistical Analysis Experiments were carried out at least 3 times (unless otherwise indicated). Where applicable, results are expressed as mean±standard deviation (SD). Student's t-test and one-way ANOVA with Bonferroni's post hoc test were used and significance reported at p ≤ 0.05. Data shown in the figures represent $p<0.01$, *$p<0.001$.

Results

Wound Healing Assay

Wound closure is an indication of both cell migration as well as proliferation of the leading edge of the wound, and a decrease of this is considered beneficial in this setting as it indicates a reduction of potential tumour growth.

FIG. 1 (A) demonstrates that CBD at 10 and 20 µM was as effective as rapamycin to block wound closer in the Tsc2−/− Mouse Embryonic Fibroblast (MEF) cell lines. Tsc2−/− MEFs have a higher capacity to close the wound than the Tsc2+/+ control cells.

FIG. 1 (B) demonstrates the data for the wound closure assays in the second cell line. CBD was effective at reducing wound closure with 5, 10 and 20 µM CBD. 20 µM CBD was as significant as rapamycin in reducing wound closure by 60%.

When CBD and rapamycin were given in combination there combined effect was similar to that of either the compounds CBD or rapamycin.

Cell Migration and Invasion Assay

Cell migration and invasion assays were carried out in the Tsc2−/− cells, using Tsc2+/+ as a control cell. There was a non-significant increase in the number of migrated cells in Tsc2−/− cells, and whilst CBD did not cause a significant reduction in these cells, it did reduce cell migration to control level as is demonstrated in FIG. 2 (A).

At concentrations of 5 µM and 10 µM, CBD had a marked effect at blocking cell invasion in the Tsc2−/− MEFs, with 5 µM CBD restoring invasion to the level of the Tsc2+/+ control cells, and 10 µM CBD having a more robust effect, as is shown in FIG. 2 (B).

In the AML 621-101 cells, CBD at both 5 µM and 10 µM was sufficient to significantly block both cell migration and invasion. Indeed, 10 µM CBD reduced cell migration to a significantly greater extent than rapamycin.

Tumour Formation Assay

Tumour formation assays were carried out in soft agar in the Tsc2−/− MEFs. Significance to inhibit tumour spheroid diameter was observed with 10 µM CBD, but not 5 µM, and with rapamycin. Similar observations were found in the AML 621-101 cells, where 10 µM was also sufficient to block tumour spheroid formation). FIG. 3 detail these data.

Western Blot Analysis

Western blotting was carried out to determine whether CBD could impair mTORC1 signalling (using rpS6 phosphorylation as a readout of mTORC1 signalling). CBD at 5 µM inhibited rpS6 phosphorylation after 6 h of treatment in the Tsc2−/− MEFs.

Under hypoxia HIF-1α protein is stabilised and ensures an angiogenic response and is necessary for tumour formation, metabolic transformation and malignancy. Of interest, CBD at 10 µM was sufficient to block hypoxia induced expression of HIF-1α protein in both Tsc2−/− MEFs and AML 621-101.

Conclusions

CBD can block tumour formation, cell migration and cell invasion in two cell models of TSC. CBD also blocks mTORC1 signalling after 6 h of treatment, and is a potent repressor of HIF-1a, which indicates that CBD could have potential as an anti-angiogenic agent.

Example 2: Efficacy of Cannabidiol in Reduction of Tumours a Zebrafish Model of Tuberous Sclerosis Complex Materials and Methods Zebrafish Husbandry A zebrafish model of TSC with a tsc2 gene deletion was used. This model has been previously published and validated (Kim et al. 2011). By mating the gene deletion animals with wild-type tsc2+/+ animals, heterozygote (tsc2+/−) zebrafish were also obtained and tested in this example.

Imaging

For both pS6 and TUNEL staining, non-consecutive sections were imaged using a Zeiss AxioImager microscope. Exposure time was kept constant during image acquisition and determined by the observation of a slide where primary antibody or enzyme solution was omitted. Pictures were taken with a 20× objective, using the AxioVision software, and coloured using Fiji ImageJ. All counting and measuring of cells was done in the original black and white pictures.

Immunohistochemistry

For TUNEL staining (1:10; Roche, Sigma, UK), 10 µm sections were cut and collected onto microscope slides, and stored at −80° C. until used. Sections were incubated for 2 hours, at room temperature, in a 2% BSA, 10% horse serum and 0.05% TX-100 buffer. After the final rinsing step, sections were incubated with TUNEL solution, in the dark, for 1 hour, at 37° C.

Negative control was performed by omitting the enzyme solution, while positive control was performed by previous incubation of sections with 5 mg/mL DNAse for 10 minutes, at 37'C.

For TUNEL assay, qualitative observation was done solely on one animal per genotype and per group, due to the low presence of labelled cells.

Statistical Analysis

Statistical analysis was performed in SPSS (IBM SPSS Statistics 22), except for the chi-square test, which was done using GraphPad Prism 5. Normality and sphericity were tested using the Kolmogorov-Smirnov and Mauchly's tests, respectively. Repeated measures two-way ANOVA tests were used to analyse the locomotor assay data and cell number, while a three-way ANOVA test was used to analyse cell size. Touch response (TR) between genotypes and treatments was analysed by chi-square test. Tests were followed by Tukey or Bonferroni post-hoc tests.

Data are expressed as mean±SEM unless stated otherwise, and significant values were considered when $p \leq 0.05$. All graphs were prepared with GraphPad Prism 5.

Materials

Pure CBD was used in this example. Danieau's solution was used as the embryo medium for the zebrafish.

Results

Cell Number:

CBD was able to decrease the number of pS6 positive cells as is shown in FIG. 4. To explore mTOR pathway activation in the different genotypes and treatments, immunohistochemistry was performed using a pS6 (Ser235/236) antibody.

Upon initial microscope observation, a stronger immunoreactivity was detected in tsc2−/− brain tissue compared to tsc2+/+ and tsc2+/− zebrafish sections. DMSO sections also showed increased reactivity when compared to the Danieau's group, while sections from CBD incubated animals showed a marked decrease in the number of pS6 positive cells.

To better understand the apparent differences between groups, pS6 positive cells were counted for each genotype and treatment. A significant main effect of genotype was found, with tsc2−/− zebrafish sections showing more pS6 positive cells in the brain than tsc2+/+ and tsc2+/−(+173.3%) (FIG. 4A).

A significant main effect of treatment was also found, indicating that CBD reduced the average number of positive cells compared to both Danieau's (−63.2%) and DMSO (−77.1%) groups. Additionally, DMSO incubated slides had a significant increase in the average number of positive cells (+61.2%) compared to Danieau's (FIG. 4B).

A significant interaction between genotype and treatment was also found, revealing that, while CBD had no significant effect on the average number of pS6 positive cells in tsc2+/+ nor tsc2+/− Danieau's incubated zebrafish, it did have a significant effect on tsc2−/− zebrafish (−55.4% for the Danieau's and −58.9% for the DMSO group) (FIG. 4C).

Cell Size

CBD decreases the area of pS6 positive cells as is shown in FIG. 5.

A significant main effect of genotype was found, indicating that tsc2−/− zebrafish had significantly larger pS6 positive brain cells than tsc2+/+ and tsc2+/−(+29%) zebrafish (FIG. 5A).

Additionally, a significant main effect of treatment was also present, revealing that CBD incubated zebrafish had smaller pS6 positive cells than the ones present in the Danieau's or DMSO groups (−20.1%) (FIG. 5B).

Finally, an interaction between genotype and treatment was found. While Danieau's incubated zebrafish had progressively bigger pS6 positive cells, according to mutation severity, DMSO incubated animals had increased pS6 positive cell size in tsc2+/+(+18.1%) but not tsc2+/− nor tsc2−/− cells, compared to the Danieau's group.

As for CBD, incubation did not affect cell size in tsc2+/+ zebrafish, but it did significantly decrease the size of pS6 positive cells in tsc2+/− and tsc2−/− zebrafish (−27.6% and −23% compared to Danieau's, and −18.1% and −20.8%, compared to the DMSO groups, respectively) (FIG. 5C).

Conclusions

The impact of CBD treatment upon the mTOR pathway was assessed by conducting immunohistochemistry against pS6, which is a commonly used marker for mTOR activity. When mTOR is active, pS6 has been shown to increase, in in vitro and in vivo models, as well as in human tissue (Roux et al. 2007).

Zebrafish with a tsc2−/− mutation exhibit more pS6 positive cells in the brain, compared to tsc2+/+ and tsc2+/− groups. The number of pS6 positive cells was not significantly different between tsc2+/+ and tsc2+/− animals.

Unexpectedly, it was found that DMSO increased the number of pS6 positive cells in the brain. However, although CBD was dissolved in this same vehicle, we saw a marked reduction in the number of pS6 positive cells in tsc2−/− zebrafish brain, compared to the other two genotypes.

Measurement of pS6 positive cells revealed that tsc2−/− cells had a larger area compared to tsc2+/+ and tsc2+/− positive cells, while these two groups did not statistically differ from each other.

When pS6 positive cell area was analysed by treatment, a significant main effect of CBD, but not of DMSO, on size was seen, revealing that CBD treated larvae had smaller cells, compared to Danieau's and DMSO treated groups.

Additionally, while the size of tsc2+/+ cells was not affected by CBD, as we had previously seen for the number of positive cells, this time, CBD also reduced the size of tsc2+/− cells, suggesting that the effect of CBD on size is mutation dependent.

In conclusion, CBD produced a positive effect in a zebrafish model of TSC, reducing both cell size and cell number of pS6 cells. This is suggestive of a disease modifying effect whereby treatment with CBD can reduce the benign tumours that occur in virtually all TSC patients.

Example 3: Efficacy of Cannabidiol in Combination with an mTOR Inhibitor in a Tumour Cell Line Materials and Methods Cell Lines PANC-1 is a human pancreatic carcinoma, epithelial-like cell line; PANC-1 cells are used as an in vitro model of non-endocrine pancreatic cancer for tumorigenicity studies. The cells possess the type B phenotype for glucose-6-phosphate dehydrogenase G6PD and overexpress heregulin/human epidermal growth-factor receptor 2 (HER2/neu) oncogene.

MIAPACA is a *Homo sapiens* pancreas carcinoma. This is a hypotriploid human cell line.

Materials

Everolimus (RAD001, Afinitor, Novartis), is a rapamycin analogue. It is an oral mammalian target of rapamycin (mTOR) inhibitor and belongs to the PI3K related family of protein kinases and is activated by phosphorylation at serine 2448 (S2448).

Pure CBD was used in this example.

Cell Viability Assay

Cell viability was analyzed by the MTT [3-(4,5-dimethylthiazol-2-yl)-2,5-diphenyl tetrazolium bromide] assay. Pancreatic cancer cells were seeded onto each well of a 96-well plate. After 72 h of treatment with CBD, MTT solution 5 mg/ml in PBS was added to each well. The plates were then incubated at 37° C. for an additional 4 h to allow MTT to form formazan crystals by reacting with metabolically active cells. The formazan crystals were solubilized in a 1N isopropanol/HCl 10% solution at 37° C., on a shaking table for 20 min. The absorbance values of the solution in each well were measured at 570 nm using a microplate reader. Cell viability was determined by the formula: cell viability (%)=(absorbance of the treated wells−absorbance of the blank control wells)/(absorbance of the negative control wells−absorbance of the blank control wells)×100%. All MTT experiments were performed in triplicate and repeated at least three times.

Drug Combination Assay

For the study of the synergism between Rad001 and CBD on pancreatic cell lines Miapaca was tested, the cells were seeded in 96-multiwell plates at the density of 3.8 $10^3$ cells/well. After 24 hr incubation at 37° C., the cells were treated with different concentrations of Rad001 and CBD. Different molar ratios between two drugs in different sequences of administration were tested, (Rad001 for 48 h and CBD for 72 h or Rad001 for 72 h and CBD for 48 h and in co-administration for 72 h.

The proliferative response was estimated by colorimetric 3-(4,5 di-methylthiazol-2-yl)-2,5-diphenyltetrazolium bromide (MTT) test. MTT conversion to formazan by metabolically viable cells was monitored by spectrophotometer at an optical density of 570 nm. Each data point represents the average of three separate experiments with each experiment containing four wells. Drug combination studies were based on concentration-effect curves generated as a plot of the fraction of unaffected (surviving) cells versus drug concentration after treatment.

To explore the relative contribution of each agent to the synergism equi-active doses of Rad001/Chloroquine were tested (IC50). Assessment of synergy was performed quantitating drug interaction by Calcusyn computer program (Biosoft, Ferguson, MO). Combination index (CI) values of <1, 1, and >1 indicate synergy, additivity and antagonism, respectively.

Dose reduction index (DRI) representing the measure of how much the dose of each drug in a combination may be reduced at a given effect level compared with the doses of each drug alone.

Potentiation Factor (PF)

The specific contribution of CBD and Rad001 on the cytotoxic effect of the combination of drugs was analysed by calculating the potentiation factor (PF) in both cell lines, defined as the ratio of the IC50 of either CBD, Rad001 alone to the IC50 of CBD and Rad001 in combination; a higher PF indicates a greater cytotoxicity Results Cell Viability Assay The growth inhibition induced by different concentrations (0.04-50 μM) of CBD on human Panc-1 at 72 h from the beginning of the treatment was evaluated with MTT assay.

In Panc-1 cells, CBD reached a 41% growth inhibition, at the concentration of 50 μM as is shown in FIG. 6A.

In Miapaca cells 50% growth inhibition was reached with CBD at the concentration of 15 μM as is shown in FIG. 6B.

Drug Combination Assay

The effects of the pharmacological combination between CBD and RAD001 on the proliferation MIAPACA cell lines, using MTT assay were studied. The data obtained were processed with dedicated program, CalcuSyn (Chou and Talalay, Biosoft, Oregon, USA), which measures synergism.

The combination of Rad001 and CBD produced a strong synergism when the drugs were administered in combination for 72 h as shown in Table 2 below.

TABLE 2

Synergy data for the combination of CBD with Rad001

| Cell line | Treatment | $CI_{50}$ | $DRI_{50}$ | Dose of drug alone | Interpretation |
|---|---|---|---|---|---|
| Miapaca | Rad/CBD combination | 0.6 ± 0.05 | Rad 2.1 CBD 7.1 | Rad 2.6 μM CBD 3.6 μM | Synergism |

Potentiation Factor (PF)

The specific contribution of CBD and Rad001 on the cytotoxic effect of the combination of drugs was analyzed by calculating the potentiation factor (PF) defined as the ratio of the IC50 of either CBD or Rad001 alone to the IC50 of CBD and Rad001 in combination. A higher PF indicates a greater cytotoxicity.

When CBD was tested in combination with Rad001, the PF for CBD was 8 and for Rad001 the PF was 4, suggesting that CBD contributed a higher degree of cytotoxicity than the mTOR inhibitor Rad001.

Conclusions

The data shown in this example demonstrates the ability of CBD to work in synergy with the mTOR inhibitor Rad001 (everolimus) in decreasing the viability of tumour cells. Such a combination may be beneficial in the treatment of TSC where mTOR inhibitors are commonly used medications.

The invention claimed is:

1. A method of reducing mTOR activity in a population of Tsc2−/− cells, comprising:
   administering from 5 μM to 20 μM cannabidiol (CBD) to the population of Tsc2−/− cells in vitro;
   wherein the CBD reduces mTOR activity in the population of Tsc2−/− cells compared to a population of Tsc2−/− cells not administered CBD.

2. The method of claim 1, wherein administering from 5 μM to 20 μM CBD reduces the number of positive phosphorylated S6 cells in the population of Tsc2−/− cells compared to a population of Tsc2−/− cells not administered CBD.

3. The method of claim 2, wherein administering from 5 μM to 50 μM CBD further reduces the cell size of pS6 positive cells in a population of Tsc2−/− cells compared to a population of Tsc2−/− cells not administered CBD.

4. The method of claim 1, wherein the CBD is administered as a highly purified extract of *cannabis* which comprises at least 95% (w/w) CBD.

5. The method of claim 4, wherein the CBD extract comprises less than 0.15% (w/w) tetrahydrocannabinol (THC).

6. The method of claim 4, wherein the CBD extract comprises up to 1% (w/w) cannabidivarin (CBDV).

7. The method of claim 1, wherein the CBD is present as a synthetic compound.

8. The method of claim 1, comprising administering CBD in DMSO.

9. The method of claim 8, wherein the DMSO is present in a composition comprising the population of Tsc2−/− cells at a maximum concentration of 0.05% (v/v).

10. The method of claim 1, comprising administering 5 μM CBD.

11. The method of claim 1, comprising administering 10 μM CBD.

12. The method of claim 1, comprising administering 20 μM CBD.

13. A method of reducing cell migration or invasion in Tsc2−/− cells, comprising:
   administering from 5 μM to 20 μM cannabidiol (CBD) to the population of Tsc2−/− cells in vitro;
   wherein the CBD reduces cell invasion or migration in the population of Tsc2−/− cells compared to a population of Tsc2−/− cells not administered CBD.

14. The method of claim 13, wherein the CBD is administered as a highly purified extract of cannabis which comprises at least 95% (w/w) CBD.

15. The method of claim 14, wherein the CBD extract comprises less than 0.15% (w/w) tetrahydrocannabinol (THC).

16. The method of claim 14, wherein the CBD extract comprises up to 1% (w/w) cannabidivarin (CBDV).

17. The method of claim 13, wherein the CBD is present as a synthetic compound.

18. The method of claim 13, comprising administering CBD in DMSO.

19. The method of claim 18, wherein the DMSO is present in a composition comprising the population of Tsc2−/− cells at a maximum concentration of 0.05% (v/v).

20. The method of claim 13, comprising administering 5 μM CBD.

21. The method of claim 13, comprising administering 10 μM CBD.

22. The method of claim 13, comprising administering 20 μM CBD.

* * * * *